United States Patent
Maksimow et al.

(10) Patent No.: US 12,371,486 B2
(45) Date of Patent: Jul. 29, 2025

(54) HUMANIZED ANTI CLEVER-1 ANTIBODIES AND THEIR USE

(71) Applicant: FARON PHARMACEUTICALS OY, Turku (FI)

(72) Inventors: Mikael Maksimow, Turku (FI); Markku Jalkanen, Piispanristi (FI); Marita Vainio, Turku (FI)

(73) Assignee: FARON PHARMACEUTICALS OY, Turku (FI)

(*) Notice: Subject to any disclaimer, the term of this patent is extended or adjusted under 35 U.S.C. 154(b) by 1033 days.

(21) Appl. No.: 17/236,684

(22) Filed: Apr. 21, 2021

(65) Prior Publication Data

US 2021/0332128 A1    Oct. 28, 2021

Related U.S. Application Data

(62) Division of application No. 16/093,257, filed as application No. PCT/FI2017/050285 on Apr. 18, 2017, now Pat. No. 11,046,761.

(30) Foreign Application Priority Data

Apr. 18, 2016  (FI) ...................................... 20165335
Apr. 18, 2016  (FI) ...................................... 20165336

(51) Int. Cl.
| | | |
|---|---|---|
| C07K 16/28 | (2006.01) | |
| A61K 39/39 | (2006.01) | |
| A61K 39/395 | (2006.01) | |
| A61P 35/00 | (2006.01) | |
| A61P 37/04 | (2006.01) | |

(52) U.S. Cl.
CPC .............. *C07K 16/28* (2013.01); *A61K 39/39* (2013.01); *A61K 39/395* (2013.01); *A61P 35/00* (2018.01); *A61P 37/04* (2018.01); *C07K 2317/34* (2013.01); *C07K 2317/76* (2013.01)

(58) Field of Classification Search
CPC .............................. C07K 16/28; A61K 39/395
See application file for complete search history.

(56) References Cited

U.S. PATENT DOCUMENTS

| | | | |
|---|---|---|---|
| 5,595,756 A | * | 1/1997 | Bally .................... A61K 9/1272 264/4.1 |
| 7,354,577 B2 | | 4/2008 | Jalkanen et al. |
| 7,910,097 B2 | | 3/2011 | Jalkanen |

FOREIGN PATENT DOCUMENTS

| | | |
|---|---|---|
| EP | 0682040 B1 | 8/1999 |
| WO | 03057130 A2 | 7/2003 |
| WO | 2006082406 A2 | 8/2006 |
| WO | 2010122217 A1 | 10/2010 |
| WO | 2014072441 A1 | 5/2014 |
| WO | 2015200806 A2 | 12/2015 |

OTHER PUBLICATIONS

Heppner et al. Tumor heterogeneity: biological implication and therapeutic consequences. Cancer Metastasis Review 2:5-23; 1983 (Year: 1983).*
Auerbach et al. ANgiogenesis assays: problems and pitfalls. Cancer and Metastasis Reviews, 2000, 19: 167-172 (Year: 2000).*
Gura T. Systems for Identifying new drugs are often faulty. Science, 1997, 278(5340): 1041-1042 (Year: 1997).*
Heppner et al. Cancer Metastasis Review 2:5-23; 1983 (Year: 1983).*
Sporn et al. Chemoprevention of Cancer, Carcinogenesis, vol. 21 (2000), 525-530 (Year: 2000).*
Auerbach et al. Cancer and Metastasis Reviews, 2000, 19: 167-172 (Year: 2000).*
Gura T. Science, 1997, 278(5340): 1041-1042 (Year: 1997).*
Jain RK. Scientific American, Jul. 1994,58-65 (Year: 1994).*
Hait. Nature Reviews/Drug Discovery, 2010, 9, pp. 253-254 (Year: 2010).*
Gravanis et al. Chin Clin Oncol, 2014, 3, pp. 1-5 (Year: 2014).*
Beans. PNAS 2018; 115(50): 12539-12543 (Year: 2018).*
First Office Action cited in Chinese Application No. 201780024478 issued Aug. 9, 2021, 20 pages.
Senthil Palani, Clever-1 as an Immune Suppressive Molecule, Mar. 18, 2016, University of Turku, 72 pages.
Vahideh Ahmadzadeh et al, "Antibody Humanization Methods for Development of Therapeutic Applications", Monoclonal Antibodies in Immunodiagnosis and Immunotherapy, vol. 33, vol. 2, 2014, 7 pages.
Office Action cited in Eurasian Patent Application No. 201892313 dated Mar. 17, 2020, 6 pages.
Stabilin-1 [*Homo sapiens*], GenBank CAB61827.1, Oct. 7, 2008, downloaded Mar. 13, 2020, 5 pages.
Coico R., Immunology: Textbook . . . , Publishing Center "Akademiya", 2008, 15 pages.
Altshuler E. P., et al., "Generation of Recombinant Antibodies and Means for Increasing Their Affinity", Uspekhi biologicheskoi khimii, vol. 50, 2010, pp. 203-258.

(Continued)

*Primary Examiner* — Vanessa L. Ford
*Assistant Examiner* — Sandra Carter
(74) *Attorney, Agent, or Firm* — ROTHWELL, FIGG, ERNST & MANBECK, P.C.

(57) ABSTRACT

This invention relates to an agent and a humanized antibody or single chain Fv or Fab fragment capable of binding to human CLEVER-1 recognizing an epitope of CLEVER-1, wherein the epitope is discontinuous and comprises the sequences: PFTVLVPSVSSFSSR and QEITVTFNQFTK. This invention relates also an agent capable of binding to an epitope of human CLEVER-1 for use in removing tumour or antigen induced immunosuppression. Further, the invention relates to a pharmaceutical composition comprising the agent capable of binding to human CLEVER-1 and an appropriate excipient.

27 Claims, 10 Drawing Sheets
Specification includes a Sequence Listing.

(56) References Cited

OTHER PUBLICATIONS

Bryson, Ch.J. et al., "Prediction of Immunogenicity of Therapeutic Proteins, Validity of Computational Tools", Biodrugs 2010, 24(1), pp. 1-8.
Kzhyshkowska, J., "Multifunctional Receptor stabilin-1 in Homeostasis and Disease", The Scientific World Journal, Mini-Review, 2010, 10, pp. 2039-2053.
Langedijk, J.P.M. et al., "Helical peptide arrays for lead identification and interaction site mapping", Analytical Biochemistry 417, 2011, pp. 149-155.
Noy, R. et al., "Tumor-Associated Macrophages: From Mechanism to Therapy", Immunity Review, 41, Jul. 17, 2014, pp. 49-61.
Perry, L.C.A. et al., "New Approaches to Prediciton of Immune Responses to Therapeutic Proteins during Preclinical Development", Drugs in R&D, 9 (6), pp. 385-396., 2008.
Timmerman, P. et al., "Functional reconstruction and synthetic mimicry of a conformational epitope using Clips TM technology", Journal of Molecular Recognition, 2007 (20), pp. 283-299.
Finnish Search Report issued in Application No. 20165336 dated Jul. 29, 2016, 3 pages.
Kzhyshkowska, J. et al., "Perspectives for Monocyte/Macrophage-Based Diagnostics of Chronic Inflammation", Transfusion Medicine and Hemotherapy, vol. 43, No. 2, Mar. 2016, pp. 66-77.
Buttari, B. et al., "7-Oxo-cholesterol potentiates pro-inflammatory signaling in human M1 and M2 macrophages", Biochemical Pharmacology, Jul. 2013, vol. 86, No. 1, pp. 130-137.
Mulens-Arias, V. et al., "Polyethylenimine-coated SPIONs trigger macrophage activation through TLR-4 signaling and ROS production and modulate podosome dynamics", Biomaterials, Jun. 2015, vol. 52, pp. 494-506.
Domínguez-Soto, A. et al., "Intravenous Immunoglobulin Promotes Antitumor Responses by Modulating Macrophage Polarization", The Journal of Immunology, Nov. 2014, vol. 193, No. 10, pp. 5181-5189.
Li, Y. et al., "Low-dose cisplatin administration to septic mice improves bacterial clearance and programs peritoneal macrophage polarization to M1 phenotype", Pathogens and Disease, Nov. 2014, vol. 72, No. 2, pp. 111-123.
Finnish Search Report issued in Application No. 20165335 dated Jul. 29, 2016, 2 pages.
International Search Report and Written Opinion issued in Application No. PCT/FI2017/050285 dated Jul. 12, 2017, 17 pages.
Palani, S. et al., "Monocyte Stabilin-1 Suppresses the Activation of Th1 Lymphocytes", Journal of Immunology, Jan. 2016, vol. 196, No. 1, pp. 115-123.
Karikoski, M. et al., "Clever-1/Stabilin-1 Controls Cancer Growth and Metastasis", Clinical Cancer Research, Dec. 2014, vol. 20, No. 24, pp. 6452-6464.
Karikoski, M. et al., "Clever-1/Stabilin-1 regulates lymphocyte migration within lymphatics and leukocyte entrance to sites of inflammation", European Journal of Immunology, Oct. 2009, vol. 39, No. 12, pp. 3477-3487.
Ahmadzadeh, V. et al., "Antibody Humanization Methods for Development of Therapeutic Applications", Monoclonal Antibodies in Immunodiagnosis and Immunotherapy, vol. 33, No. 2, Apr. 1, 2014, pp. 67-73.
Holgate, R. et al., "Circumventing immunogenicity in the development of therapeutic antibodies", IDrugs, 2009, vol. 12, No. 4, pp. 233-237.
Palani, S. et al., "Stabilin-1/CLEVER-1, a type 2 macrophage marker, is an adhesion and scavenging molecule on human placental macrophages: Innate Immunity", European Journal of Immunology, vol. 41, No. 7, Jul. 1, 2011, pp. 2052-2063.
Palani, S. "Clever-1 as an Immune Suppresive Molecule", University of Turku, Mar. 18, 2016, XP055384491, pp. 1-72.
Hollmén et al., "New tools to prevent cancer growth and spread: a 'Clever' approach" (2020) Br J Cancer 123(4):501-09.
Rannikko et al., "Bexmarilimab-induced macrophage activation leads to treatment benefit in solid tumors: The phase I/II first-in-human Matins trial" (2023) Cell Reports Med. 4:101307, 18 pages.
Viitala et al., "Immunotherapeutic Blockade of Macrophage Clever-1 Reactivates the CD8+ T-cell Response against Immunosuppressive Tumors" (2019) Clin. Cancer Res. 25(11):3289-3303.

* cited by examiner

SEQUENCE LISTING

```
<160> NUMBER OF SEQ ID NOS: 35

<210> SEQ ID NO 1
<211> LENGTH: 15
<212> TYPE: PRT
<213> ORGANISM: Homo sapiens

<400> SEQUENCE: 1

Pro Phe Thr Val Leu Val Pro Ser Val Ser Ser Phe Ser Ser Arg
1               5                   10                  15

<210> SEQ ID NO 2
<211> LENGTH: 12
<212> TYPE: PRT
<213> ORGANISM: Homo sapiens

<400> SEQUENCE: 2

Gln Glu Ile Thr Val Thr Phe Asn Gln Phe Thr Lys
1               5                   10

<210> SEQ ID NO 3
<211> LENGTH: 10
<212> TYPE: PRT
<213> ORGANISM: Homo sapiens

<400> SEQUENCE: 3
```

```
Ala Thr Gln Thr Gly Arg Val Phe Leu Gln
1               5                   10

<210> SEQ ID NO 4
<211> LENGTH: 12
<212> TYPE: PRT
<213> ORGANISM: Homo sapiens

<400> SEQUENCE: 4

Asp Ser Leu Arg Asp Gly Arg Leu Ile Tyr Leu Phe
1               5                   10

<210> SEQ ID NO 5
<211> LENGTH: 13
<212> TYPE: PRT
<213> ORGANISM: Homo sapiens

<400> SEQUENCE: 5

Ser Lys Gly Arg Ile Leu Thr Met Ala Asn Gln Val Leu
1               5                   10

<210> SEQ ID NO 6
<211> LENGTH: 15
<212> TYPE: PRT
<213> ORGANISM: Homo sapiens

<400> SEQUENCE: 6

Leu Cys Val Tyr Gln Lys Pro Gly Gln Ala Phe Cys Thr Cys Arg
1               5                   10                  15

<210> SEQ ID NO 7
<211> LENGTH: 7
<212> TYPE: PRT
<213> ORGANISM: Artificial sequence
<220> FEATURE:
<223> OTHER INFORMATION: Heavy Chain CDR

<400> SEQUENCE: 7

Thr Ser Gly Met Gly Ile Gly
1               5

<210> SEQ ID NO 8
<211> LENGTH: 16
<212> TYPE: PRT
<213> ORGANISM: Artificial sequence
<220> FEATURE:
<223> OTHER INFORMATION: Heavy Chain CDR

<400> SEQUENCE: 8

His Ile Trp Trp Asp Asp Lys Arg Tyr Asn Pro Ala Leu Lys Ser
1               5                   10                  15

<210> SEQ ID NO 9
<211> LENGTH: 12
<212> TYPE: PRT
<213> ORGANISM: Artificial sequence
<220> FEATURE:
<223> OTHER INFORMATION: Heavy Chain CDR

<400> SEQUENCE: 9

His Tyr Gly Tyr Asp Pro Tyr Tyr Ala Met Asp Tyr
1               5                   10

<210> SEQ ID NO 10
<211> LENGTH: 12
<212> TYPE: PRT
```

-continued

<213> ORGANISM: Artificial sequence
<220> FEATURE:
<223> OTHER INFORMATION: Light Chain CDR

<400> SEQUENCE: 10

Thr Ala Ser Ser Ser Val Ser Ser Ser Tyr Leu His
1               5                   10

<210> SEQ ID NO 11
<211> LENGTH: 7
<212> TYPE: PRT
<213> ORGANISM: Artificial sequence
<220> FEATURE:
<223> OTHER INFORMATION: Light Chain CDR

<400> SEQUENCE: 11

Arg Thr Ser Asn Leu Ala Ser
1               5

<210> SEQ ID NO 12
<211> LENGTH: 9
<212> TYPE: PRT
<213> ORGANISM: Artificial sequence
<220> FEATURE:
<223> OTHER INFORMATION: Light Chain CDR

<400> SEQUENCE: 12

His Gln Tyr His Arg Ser Pro Pro Thr
1               5

<210> SEQ ID NO 13
<211> LENGTH: 366
<212> TYPE: DNA
<213> ORGANISM: Artificial sequence
<220> FEATURE:
<223> OTHER INFORMATION: Heavy Chain
<220> FEATURE:
<221> NAME/KEY: CDS
<222> LOCATION: (1)..(366)

<400> SEQUENCE: 13

```
cag gtc aca ctg aaa gag tcc ggc ccc acc atc gtg aag ccc acc cag      48
Gln Val Thr Leu Lys Glu Ser Gly Pro Thr Ile Val Lys Pro Thr Gln
1               5                   10                  15 acc ctg acc ctg aca tgc agc ttc agc ggc ttc agc ctg aac acc agc      96
Thr Leu Thr Leu Thr Cys Ser Phe Ser Gly Phe Ser Leu Asn Thr Ser
            20                  25                  30 ggc atg ggc atc ggc tgg atc aga cag ccc agc ggc aag gcc ctg gaa     144
Gly Met Gly Ile Gly Trp Ile Arg Gln Pro Ser Gly Lys Ala Leu Glu
        35                  40                  45 tgg ctg gcc cac att tgg tgg gac gac gac aag cgg tac aac ccc gcc     192
Trp Leu Ala His Ile Trp Trp Asp Asp Asp Lys Arg Tyr Asn Pro Ala
    50                  55                  60 ctg aag tcc cgg ctg acc atc agc aag gac acc agc aag aac cag gtg     240
Leu Lys Ser Arg Leu Thr Ile Ser Lys Asp Thr Ser Lys Asn Gln Val
65                  70                  75                  80 gtg ctg acc atg acc aac atg gac ccc gtg gac acc gcc acc tac tac     288
Val Leu Thr Met Thr Asn Met Asp Pro Val Asp Thr Ala Thr Tyr Tyr
                85                  90                  95 tgc gcc aga cac tac ggc tac gac ccc tac tac gcc atg gac tac tgg     336
Cys Ala Arg His Tyr Gly Tyr Asp Pro Tyr Tyr Ala Met Asp Tyr Trp
            100                 105                 110 ggc cag ggc acc agc gtg acc gtg tct agc                             366
Gly Gln Gly Thr Ser Val Thr Val Ser Ser
        115                 120
```

<210> SEQ ID NO 14
<211> LENGTH: 122
<212> TYPE: PRT
<213> ORGANISM: Artificial sequence
<220> FEATURE:
<223> OTHER INFORMATION: Heavy Chain

<400> SEQUENCE: 14

Gln Val Thr Leu Lys Glu Ser Gly Pro Thr Ile Val Lys Pro Thr Gln
1               5                   10                  15

Thr Leu Thr Leu Thr Cys Ser Phe Ser Gly Phe Ser Leu Asn Thr Ser
            20                  25                  30

Gly Met Gly Ile Gly Trp Ile Arg Gln Pro Ser Gly Lys Ala Leu Glu
        35                  40                  45

Trp Leu Ala His Ile Trp Trp Asp Asp Asp Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg His Tyr Gly Tyr Asp Pro Tyr Tyr Ala Met Asp Tyr Trp
            100                 105                 110

Gly Gln Gly Thr Leu Val Thr Val Ser Ser
        115                 120

<210> SEQ ID NO 15
<211> LENGTH: 366
<212> TYPE: DNA
<213> ORGANISM: Artificial sequence
<220> FEATURE:
<223> OTHER INFORMATION: Heavy Chain
<220> FEATURE:
<221> NAME/KEY: CDS
<222> LOCATION: (1)..(366)

<400> SEQUENCE: 15

```
cag gtc aca ctg aaa gag tcc ggc ccc acc ctg gtg aag ccc acc cag        48
Gln Val Thr Leu Lys Glu Ser Gly Pro Thr Leu Val Lys Pro Thr Gln
1               5                   10                  15 acc ctg acc ctg aca tgc agc ttc agc ggc ttc agc ctg agc acc agc        96
Thr Leu Thr Leu Thr Cys Ser Phe Ser Gly Phe Ser Leu Ser Thr Ser
            20                  25                  30 ggc atg ggc atc gga tgg atc aga cag ccc agc ggc aag gcc ctg gaa       144
Gly Met Gly Ile Gly Trp Ile Arg Gln Pro Ser Gly Lys Ala Leu Glu
        35                  40                  45 tgg ctg gcc cac att tgg tgg gac gac gac aag cgg tac aac ccc gcc       192
Trp Leu Ala His Ile Trp Trp Asp Asp Asp Lys Arg Tyr Asn Pro Ala
    50                  55                  60 ctg aag tcc cgg ctg acc atc agc aag gac acc agc aag aac cag gtg       240
Leu Lys Ser Arg Leu Thr Ile Ser Lys Asp Thr Ser Lys Asn Gln Val
65                  70                  75                  80 gtg ctg acc atg acc aac atg gac ccc gtg gac acc gcc acc tac tac       288
Val Leu Thr Met Thr Asn Met Asp Pro Val Asp Thr Ala Thr Tyr Tyr
                85                  90                  95 tgc gcc aga cac tac ggc tac gac ccc tac tac gcc atg gac tac tgg       336
Cys Ala Arg His Tyr Gly Tyr Asp Pro Tyr Tyr Ala Met Asp Tyr Trp
            100                 105                 110 ggc cag ggc acc ctc gtg acc gtg tct agc                               366
Gly Gln Gly Thr Leu Val Thr Val Ser Ser
        115                 120
```

```
<210> SEQ ID NO 16
<211> LENGTH: 122
<212> TYPE: PRT
<213> ORGANISM: Artificial sequence
<220> FEATURE:
<223> OTHER INFORMATION: Heavy Chain

<400> SEQUENCE: 16

Gln Val Thr Leu Lys Glu Ser Gly Pro Thr Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Met Gly Ile Gly Trp Ile Arg Gln Pro Ser Gly Lys Ala Leu Glu
        35                  40                  45

Trp Leu Ala His Ile Trp Trp Asp Asp Asp Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg His Tyr Gly Tyr Asp Pro Tyr Tyr Ala Met Asp Tyr Trp
            100                 105                 110

Gly Gln Gly Thr Leu Val Thr Val Ser Ser
        115                 120

<210> SEQ ID NO 17
<211> LENGTH: 366
<212> TYPE: DNA
<213> ORGANISM: Artificial sequence
<220> FEATURE:
<223> OTHER INFORMATION: Heavy Chain
<220> FEATURE:
<221> NAME/KEY: CDS
<222> LOCATION: (1)..(366)

<400> SEQUENCE: 17 cag gtc aca ctg aaa gag tcc ggc ccc acc ctg gtg aag ccc acc cag    48
Gln Val Thr Leu Lys Glu Ser Gly Pro Thr Leu Val Lys Pro Thr Gln
1               5                   10                  15 acc ctg acc ctg aca tgc agc ttc agc ggc ttc agc ctg agc acc agc    96
Thr Leu Thr Leu Thr Cys Ser Phe Ser Gly Phe Ser Leu Ser Thr Ser
            20                  25                  30 ggc atg ggc atc gga tgg atc aga cag ccc cct ggc aag gcc ctg gaa   144
Gly Met Gly Ile Gly Trp Ile Arg Gln Pro Pro Gly Lys Ala Leu Glu
        35                  40                  45 tgg ctg gcc cac att tgg tgg gac gac gac aag cgg tac aac ccc gcc   192
Trp Leu Ala His Ile Trp Trp Asp Asp Asp Lys Arg Tyr Asn Pro Ala
    50                  55                  60 ctg aag tcc cgg ctg acc atc agc aag gac acc agc aag aac cag gtg   240
Leu Lys Ser Arg Leu Thr Ile Ser Lys Asp Thr Ser Lys Asn Gln Val
65                  70                  75                  80 gtg ctg acc atg acc aac atg gac ccc gtg gac acc gcc acc tac tac   288
Val Leu Thr Met Thr Asn Met Asp Pro Val Asp Thr Ala Thr Tyr Tyr
                85                  90                  95 tgc gcc aga cac tac ggc tac gac ccc tac tac gcc atg gac tac tgg   336
Cys Ala Arg His Tyr Gly Tyr Asp Pro Tyr Tyr Ala Met Asp Tyr Trp
            100                 105                 110 ggc cag ggc acc ctc gtg acc gtg tct agc                            366
Gly Gln Gly Thr Leu Val Thr Val Ser Ser
        115                 120
```

```
<210> SEQ ID NO 18
<211> LENGTH: 122
<212> TYPE: PRT
<213> ORGANISM: Artificial sequence
<220> FEATURE:
<223> OTHER INFORMATION: Heavy Chain

<400> SEQUENCE: 18

Gln Val Thr Leu Lys Glu Ser Gly Pro Thr Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Met Gly Ile Gly Trp Ile Arg Gln Pro Pro Gly Lys Ala Leu Glu
        35                  40                  45

Trp Leu Ala His Ile Trp Trp Asp Asp Asp Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg His Tyr Gly Tyr Asp Pro Tyr Tyr Ala Met Asp Tyr Trp
            100                 105                 110

Gly Gln Gly Thr Leu Val Thr Val Ser Ser
        115                 120

<210> SEQ ID NO 19
<211> LENGTH: 366
<212> TYPE: DNA
<213> ORGANISM: Artificial sequence
<220> FEATURE:
<223> OTHER INFORMATION: Heavy Chain
<220> FEATURE:
<221> NAME/KEY: CDS
<222> LOCATION: (1)..(366)

<400> SEQUENCE: 19 cag gtc aca ctg aaa gag tcc ggc ccc acc ctg gtg aag ccc acc cag      48
Gln Val Thr Leu Lys Glu Ser Gly Pro Thr Leu Val Lys Pro Thr Gln
1               5                   10                  15 acc ctg acc ctg aca tgc acc ttc agc ggc ttc agc ctg agc acc agc      96
Thr Leu Thr Leu Thr Cys Thr Phe Ser Gly Phe Ser Leu Ser Thr Ser
            20                  25                  30 ggc atg ggc atc gga tgg atc aga cag ccc cct ggc aag gcc ctg gaa     144
Gly Met Gly Ile Gly Trp Ile Arg Gln Pro Pro Gly Lys Ala Leu Glu
        35                  40                  45 tgg ctg gcc cac att tgg tgg gac gac gac aag cgg tac aac ccc gcc     192
Trp Leu Ala His Ile Trp Trp Asp Asp Asp Lys Arg Tyr Asn Pro Ala
    50                  55                  60 ctg aag tcc cgg ctg acc atc agc aag gac acc agc aag aac cag gtg     240
Leu Lys Ser Arg Leu Thr Ile Ser Lys Asp Thr Ser Lys Asn Gln Val
65                  70                  75                  80 gtg ctk acc atg acc aac atg gac ccc gtg gac acc gcc acc tac tac     288
Val Xaa Thr Met Thr Asn Met Asp Pro Val Asp Thr Ala Thr Tyr Tyr
                85                  90                  95 tgc gcc aga cac tac ggc tac gac ccc tac tac gcc atg gac tac tgg     336
Cys Ala Arg His Tyr Gly Tyr Asp Pro Tyr Tyr Ala Met Asp Tyr Trp
            100                 105                 110 ggc cag ggc acc ctc gtg acc gtg tct agc                             366
Gly Gln Gly Thr Leu Val Thr Val Ser Ser
        115                 120
```

<210> SEQ ID NO 20
<211> LENGTH: 122
<212> TYPE: PRT
<213> ORGANISM: Artificial sequence
<220> FEATURE:
<223> OTHER INFORMATION: Heavy Chain
<220> FEATURE:
<221> NAME/KEY: misc_feature
<222> LOCATION: (82)..(82)
<223> OTHER INFORMATION: The 'Xaa' at location 82 stands for Leu.

<400> SEQUENCE: 20

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Ile Gly Trp Ile Arg Gln Pro Pro Gly Lys Ala Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Xaa Thr Met Thr Asn Met Asp Pro Val Asp Thr Ala Thr Tyr Tyr
                85                  90                  95

Cys Ala Arg His Tyr Gly Tyr Asp Pro Tyr Tyr Ala Met Asp Tyr Trp
            100                 105                 110

Gly Gln Gly Thr Leu Val Thr Val Ser Ser
        115                 120

<210> SEQ ID NO 21
<211> LENGTH: 324
<212> TYPE: DNA
<213> ORGANISM: Artificial sequence
<220> FEATURE:
<223> OTHER INFORMATION: Light Chain
<220> FEATURE:
<221> NAME/KEY: CDS
<222> LOCATION: (1)..(324)

<400> SEQUENCE: 21 cag atc gtg ctg acc cag agc ccc ggc atc ctg tct ctg agc cct ggc      48
Gln Ile Val Leu Thr Gln Ser Pro Gly Ile Leu Ser Leu Ser Pro Gly
1               5                   10                  15 gag agg gcc acc atg agc tgt acc gcc agc agc agc gtg tcc tcc agc      96
Glu Arg Ala Thr Met Ser Cys Thr Ala Ser Ser Ser Val Ser Ser Ser
            20                  25                  30 tac ctg cac tgg tat cag cag aag ccc ggc aag gcc ccc aag ctg tgc     144
Tyr Leu His Trp Tyr Gln Gln Lys Pro Gly Lys Ala Pro Lys Leu Cys
        35                  40                  45 atc tac cgg acc agc aac ctg gcc agc ggc gtg ccc agc aga ttt tct     192
Ile Tyr Arg Thr Ser Asn Leu Ala Ser Gly Val Pro Ser Arg Phe Ser
    50                  55                  60 ggc agc ggc agc ggc acc gac tac acc ctg acc atc agc agc ctg cag     240
Gly Ser Gly Ser Gly Thr Asp Tyr Thr Leu Thr Ile Ser Ser Leu Gln
65                  70                  75                  80 gcc gag gac ttc gcc acc tac tac tgc cac cag tac cac aga agc ccc     288
Ala Glu Asp Phe Ala Thr Tyr Tyr Cys His Gln Tyr His Arg Ser Pro
                85                  90                  95 ccc acc ttc ggc cag ggc acc aaa ctg gaa atc aag                     324
Pro Thr Phe Gly Gln Gly Thr Lys Leu Glu Ile Lys
            100                 105

<210> SEQ ID NO 22
<211> LENGTH: 108
<212> TYPE: PRT
<213> ORGANISM: Artificial sequence
<220> FEATURE:
<223> OTHER INFORMATION: Light Chain

<400> SEQUENCE: 22

```
Gln Ile Val Leu Thr Gln Ser Pro Gly Ile Leu Ser Leu Ser Pro Gly
1               5                   10                  15

Glu Arg Ala Thr Met Ser Cys Thr Ala Ser Ser Val Ser Ser
            20                  25                  30

Tyr Leu His Trp Tyr Gln Gln Lys Pro Gly Lys Ala Pro Lys Leu Cys
            35                  40                  45

Ile Tyr Arg Thr Ser Asn Leu Ala Ser Gly Val Pro Ser Arg Phe Ser
        50                  55                  60

Gly Ser Gly Ser Gly Thr Asp Tyr Thr Leu Thr Ile Ser Ser Leu Gln
65                  70                  75                  80

Ala Glu Asp Phe Ala Thr Tyr Tyr Cys His Gln Tyr His Arg Ser Pro
                85                  90                  95

Pro Thr Phe Gly Gln Gly Thr Lys Leu Glu Ile Lys
            100                 105
```

<210> SEQ ID NO 23
<211> LENGTH: 324
<212> TYPE: DNA
<213> ORGANISM: Artificial sequence
<220> FEATURE:
<223> OTHER INFORMATION: Light Chain
<220> FEATURE:
<221> NAME/KEY: CDS
<222> LOCATION: (1)..(324)

<400> SEQUENCE: 23

```
cag atc gtg ctg acc cag agc ccc ggc acc ctg tct ctg agc cct ggc        48
Gln Ile Val Leu Thr Gln Ser Pro Gly Thr Leu Ser Leu Ser Pro Gly
1               5                   10                  15 gag agg gcc acc atg agc tgt acc gcc agc agc agc gtg tcc tcc agc        96
Glu Arg Ala Thr Met Ser Cys Thr Ala Ser Ser Ser Val Ser Ser
            20                  25                  30 tac ctg cac tgg tat cag cag aag ccc ggc aag gcc ccc aag ctg tgc       144
Tyr Leu His Trp Tyr Gln Gln Lys Pro Gly Lys Ala Pro Lys Leu Cys
            35                  40                  45 atc tac cgg acc agc aac ctg gcc agc ggc gtg ccc agc aga ttt tct       192
Ile Tyr Arg Thr Ser Asn Leu Ala Ser Gly Val Pro Ser Arg Phe Ser
        50                  55                  60 ggc agc ggc agc ggc acc gac tac acc ctg acc atc agc agc ctg cag       240
Gly Ser Gly Ser Gly Thr Asp Tyr Thr Leu Thr Ile Ser Ser Leu Gln
65                  70                  75                  80 ccc gag gac ttc gcc acc tac tac tgc cac cag tac cac aga agc ccc       288
Pro Glu Asp Phe Ala Thr Tyr Tyr Cys His Gln Tyr His Arg Ser Pro
                85                  90                  95 ccc acc ttc ggc cag ggc acc aaa ctg gaa atc aag                       324
Pro Thr Phe Gly Gln Gly Thr Lys Leu Glu Ile Lys
            100                 105
```

<210> SEQ ID NO 24
<211> LENGTH: 108
<212> TYPE: PRT
<213> ORGANISM: Artificial sequence
<220> FEATURE:

<223> OTHER INFORMATION: Light Chain

<400> SEQUENCE: 24

```
Gln Ile Val Leu Thr Gln Ser Pro Gly Thr Leu Ser Leu Ser Pro Gly
1               5                   10                  15
Glu Arg Ala Thr Met Ser Cys Thr Ala Ser Ser Val Ser Ser Ser
            20                  25                  30
Tyr Leu His Trp Tyr Gln Gln Lys Pro Gly Lys Ala Pro Lys Leu Cys
        35                  40                  45
Ile Tyr Arg Thr Ser Asn Leu Ala Ser Gly Val Pro Ser Arg Phe Ser
    50                  55                  60
Gly Ser Gly Ser Gly Thr Asp Tyr Thr Leu Thr Ile Ser Ser Leu Gln
65                  70                  75                  80
Pro Glu Asp Phe Ala Thr Tyr Tyr Cys His Gln Tyr His Arg Ser Pro
                85                  90                  95
Pro Thr Phe Gly Gln Gly Thr Lys Leu Glu Ile Lys
            100                 105
```

<210> SEQ ID NO 25
<211> LENGTH: 324
<212> TYPE: DNA
<213> ORGANISM: Artificial sequence
<220> FEATURE:
<223> OTHER INFORMATION: Light Chain
<220> FEATURE:
<221> NAME/KEY: CDS
<222> LOCATION: (1)..(324)

<400> SEQUENCE: 25

```
gag atc gtg ctg acc cag agc ccc ggc acc ctg tct ctg agc cct ggc      48
Glu Ile Val Leu Thr Gln Ser Pro Gly Thr Leu Ser Leu Ser Pro Gly
1               5                   10                  15 gag agg gcc acc atg agc tgt acc gcc agc agc agc gtg tcc tcc agc      96
Glu Arg Ala Thr Met Ser Cys Thr Ala Ser Ser Ser Val Ser Ser Ser
            20                  25                  30 tac ctg cac tgg tat cag cag aag ccc ggc aag gcc ccc aag ctg tgc     144
Tyr Leu His Trp Tyr Gln Gln Lys Pro Gly Lys Ala Pro Lys Leu Cys
        35                  40                  45 atc tac cgg acc agc aac ctg gcc agc ggc gtg ccc agc aga ttt tct     192
Ile Tyr Arg Thr Ser Asn Leu Ala Ser Gly Val Pro Ser Arg Phe Ser
    50                  55                  60 ggc agc ggc agc ggc acc gac tac acc ctg acc atc agc agc ctg cag     240
Gly Ser Gly Ser Gly Thr Asp Tyr Thr Leu Thr Ile Ser Ser Leu Gln
65                  70                  75                  80 ccc gag gac ttc gcc acc tac tac tgc cac cag tac cac aga agc ccc     288
Pro Glu Asp Phe Ala Thr Tyr Tyr Cys His Gln Tyr His Arg Ser Pro
                85                  90                  95 ccc acc ttc ggc cag ggc acc aaa ctg gaa atc aag                     324
Pro Thr Phe Gly Gln Gly Thr Lys Leu Glu Ile Lys
            100                 105
```

<210> SEQ ID NO 26
<211> LENGTH: 108
<212> TYPE: PRT
<213> ORGANISM: Artificial sequence
<220> FEATURE:
<223> OTHER INFORMATION: Light Chain

<400> SEQUENCE: 26

```
Glu Ile Val Leu Thr Gln Ser Pro Gly Thr Leu Ser Leu Ser Pro Gly
1               5                   10                  15
```

```
Glu Arg Ala Thr Met Ser Cys Thr Ala Ser Ser Ser Val Ser Ser
            20                  25                  30

Tyr Leu His Trp Tyr Gln Gln Lys Pro Gly Lys Ala Pro Lys Leu Cys
        35                  40                  45

Ile Tyr Arg Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Pro Thr Phe Gly Gln Gly Thr Lys Leu Glu Ile Lys
            100                 105
```

```
<210> SEQ ID NO 27
<211> LENGTH: 324
<212> TYPE: DNA
<213> ORGANISM: Artificial sequence
<220> FEATURE:
<223> OTHER INFORMATION: Light Chain
<220> FEATURE:
<221> NAME/KEY: CDS
<222> LOCATION: (1)..(324)

<400> SEQUENCE: 27
```

```
cag atc gtg ctg acc cag agc ccc ggc atc ctg tct ctg agc cct ggc       48
Gln Ile Val Leu Thr Gln Ser Pro Gly Ile Leu Ser Leu Ser Pro Gly
1               5                   10                  15 gag agg gcc acc atg agc tgt acc gcc agc agc agc gtg tcc tcc agc       96
Glu Arg Ala Thr Met Ser Cys Thr Ala Ser Ser Ser Val Ser Ser Ser
            20                  25                  30 tac ctg cac tgg tat cag cag aag ccc ggc aag gcc ccc aag ctg ctg      144
Tyr Leu His Trp Tyr Gln Gln Lys Pro Gly Lys Ala Pro Lys Leu Leu
        35                  40                  45 atc tac cgg acc agc aac ctg gcc agc ggc gtg ccc agc aga ttt tct      192
Ile Tyr Arg Thr Ser Asn Leu Ala Ser Gly Val Pro Ser Arg Phe Ser
    50                  55                  60 ggc agc ggc agc ggc acc gac tac acc ctg acc atc agc agc ctg cag      240
Gly Ser Gly Ser Gly Thr Asp Tyr Thr Leu Thr Ile Ser Ser Leu Gln
65                  70                  75                  80 gcc gag gac ttc gcc acc tac tac tgc cac cag tac cac aga agc ccc      288
Ala Glu Asp Phe Ala Thr Tyr Tyr Cys His Gln Tyr His Arg Ser Pro
                85                  90                  95 ccc acc ttc ggc cag ggc acc aaa ctg gaa atc aag                      324
Pro Thr Phe Gly Gln Gly Thr Lys Leu Glu Ile Lys
            100                 105
```

```
<210> SEQ ID NO 28
<211> LENGTH: 108
<212> TYPE: PRT
<213> ORGANISM: Artificial sequence
<220> FEATURE:
<223> OTHER INFORMATION: Light Chain

<400> SEQUENCE: 28
```

```
Gln Ile Val Leu Thr Gln Ser Pro Gly Ile Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Leu His Trp Tyr Gln Gln Lys Pro Gly Lys Ala Pro Lys Leu Leu
        35                  40                  45

Ile Tyr Arg Thr Ser Asn Leu Ala Ser Gly Val Pro Ser Arg Phe Ser
```

```
                    50                  55                  60
Gly Ser Gly Ser Gly Thr Asp Tyr Thr Leu Thr Ile Ser Ser Leu Gln
 65                  70                  75                  80

Ala Glu Asp Phe Ala Thr Tyr Tyr Cys His Gln Tyr His Arg Ser Pro
                 85                  90                  95

Pro Thr Phe Gly Gln Gly Thr Lys Leu Glu Ile Lys
            100                 105

<210> SEQ ID NO 29
<211> LENGTH: 324
<212> TYPE: DNA
<213> ORGANISM: Artificial sequence
<220> FEATURE:
<223> OTHER INFORMATION: Light Chain
<220> FEATURE:
<221> NAME/KEY: CDS
<222> LOCATION: (1)..(324)

<400> SEQUENCE: 29 gag atc gtg ctg acc cag agc ccc ggc acc ctg tct ctg agc cct ggc      48
Glu Ile Val Leu Thr Gln Ser Pro Gly Thr Leu Ser Leu Ser Pro Gly
 1               5                  10                  15 gag agg gcc acc ctg agc tgt acc gcc agc agc agc gtg tcc tcc agc      96
Glu Arg Ala Thr Leu Ser Cys Thr Ala Ser Ser Ser Val Ser Ser Ser
             20                  25                  30 tac ctg cac tgg tat cag cag aag ccc ggc aag gcc ccc aag ctg ctg     144
Tyr Leu His Trp Tyr Gln Gln Lys Pro Gly Lys Ala Pro Lys Leu Leu
         35                  40                  45 atc tac cgg acc agc aac ctg gcc agc ggc gtg ccc agc aga ttt tct     192
Ile Tyr Arg Thr Ser Asn Leu Ala Ser Gly Val Pro Ser Arg Phe Ser
     50                  55                  60 ggc agc ggc agc ggc acc gac tac acc ctg acc atc agc agc ctg cag     240
Gly Ser Gly Ser Gly Thr Asp Tyr Thr Leu Thr Ile Ser Ser Leu Gln
 65                  70                  75                  80 ccc gag gac ttc gcc acc tac tac tgc cac cag tac cac aga agc ccc     288
Pro Glu Asp Phe Ala Thr Tyr Tyr Cys His Gln Tyr His Arg Ser Pro
                 85                  90                  95 ccc acc ttc ggc cag ggc acc aaa ctg gaa atc aag                     324
Pro Thr Phe Gly Gln Gly Thr Lys Leu Glu Ile Lys
            100                 105

<210> SEQ ID NO 30
<211> LENGTH: 108
<212> TYPE: PRT
<213> ORGANISM: Artificial sequence
<220> FEATURE:
<223> OTHER INFORMATION: Light Chain

<400> SEQUENCE: 30

Glu Ile Val Leu Thr Gln Ser Pro Gly Thr Leu Ser Leu Ser Pro Gly
 1               5                  10                  15

Glu Arg Ala Thr Leu Ser Cys Thr Ala Ser Ser Ser Val Ser Ser Ser
             20                  25                  30

Tyr Leu His Trp Tyr Gln Gln Lys Pro Gly Lys Ala Pro Lys Leu Leu
         35                  40                  45

Ile Tyr Arg Thr Ser Asn Leu Ala Ser Gly Val Pro Ser Arg Phe Ser
     50                  55                  60

Gly Ser Gly Ser Gly Thr Asp Tyr Thr Leu Thr Ile Ser Ser Leu Gln
 65                  70                  75                  80

Pro Glu Asp Phe Ala Thr Tyr Tyr Cys His Gln Tyr His Arg Ser Pro
                 85                  90                  95
```

```
Pro Thr Phe Gly Gln Gly Thr Lys Leu Glu Ile Lys
            100                 105
```

<210> SEQ ID NO 31
<211> LENGTH: 1051
<212> TYPE: PRT
<213> ORGANISM: Homo sapiens

<400> SEQUENCE: 31

```
Leu Cys Cys Ala Cys Leu Leu Glu Leu Ile Pro Tyr Ala Pro Thr Leu
1               5                   10                  15

Ser Trp Thr Ala Cys Pro Pro Ala Met Ala Gly Pro Arg Gly Leu Leu
            20                  25                  30

Pro Leu Cys Leu Leu Ala Phe Cys Leu Ala Gly Phe Ser Phe Val Arg
        35                  40                  45

Gly Gln Val Leu Phe Lys Gly Cys Asp Val Lys Thr Thr Phe Val Thr
    50                  55                  60

His Val Pro Cys Thr Ser Cys Ala Ala Ile Lys Lys Gln Thr Cys Pro
65                  70                  75                  80

Ser Gly Trp Leu Arg Glu Leu Pro Asp Gln Ile Thr Gln Asp Cys Arg
                85                  90                  95

Tyr Glu Val Gln Leu Gly Gly Ser Met Val Ser Met Ser Gly Cys Arg
            100                 105                 110

Arg Lys Cys Arg Lys Gln Val Val Gln Lys Ala Cys Cys Pro Gly Tyr
        115                 120                 125

Trp Gly Ser Arg Cys His Glu Cys Pro Gly Ala Glu Thr Pro Cys
    130                 135                 140

Asn Gly His Gly Thr Cys Leu Asp Gly Met Asp Arg Asn Gly Thr Cys
145                 150                 155                 160

Val Cys Gln Glu Asn Phe Arg Gly Ser Ala Cys Gln Glu Cys Gln Asp
                165                 170                 175

Pro Asn Arg Phe Gly Pro Asp Cys Gln Ser Val Cys Ser Cys Val His
            180                 185                 190

Gly Val Cys Asn His Gly Pro Arg Gly Asp Gly Ser Cys Leu Cys Phe
        195                 200                 205

Ala Gly Tyr Thr Gly Pro His Cys Asp Gln Glu Leu Pro Val Cys Gln
    210                 215                 220

Glu Leu Arg Cys Pro Gln Asn Thr Gln Cys Ser Ala Glu Ala Pro Ser
225                 230                 235                 240

Cys Arg Cys Leu Pro Gly Tyr Thr Gln Gly Ser Glu Cys Arg Ala
                245                 250                 255

Pro Asn Pro Cys Trp Pro Ser Pro Cys Ser Leu Leu Ala Gln Cys Ser
            260                 265                 270

Val Ser Pro Lys Gly Gln Ala Gln Cys His Cys Pro Glu Asn Tyr His
        275                 280                 285

Gly Asp Gly Met Val Cys Leu Pro Lys Asp Pro Cys Thr Asp Asn Leu
    290                 295                 300

Gly Gly Cys Pro Ser Asn Ser Thr Leu Cys Val Tyr Gln Lys Pro Gly
305                 310                 315                 320

Gln Ala Phe Cys Thr Cys Arg Pro Gly Leu Val Ser Ile Asn Ser Asn
                325                 330                 335

Ala Ser Ala Gly Cys Phe Ala Phe Cys Ser Pro Phe Ser Cys Asp Arg
            340                 345                 350

Ser Ala Thr Cys Gln Val Thr Ala Asp Gly Lys Thr Ser Cys Val Cys
```

```
            355                 360                 365
Arg Glu Ser Glu Val Gly Asp Gly Arg Ala Cys Tyr Gly His Leu Leu
370                 375                 380

His Glu Val Gln Lys Ala Thr Gln Thr Gly Arg Val Phe Leu Gln Leu
385                 390                 395                 400

Arg Val Ala Val Ala Met Met Asp Gln Gly Cys Arg Glu Ile Leu Thr
                405                 410                 415

Thr Ala Gly Pro Phe Thr Val Leu Val Pro Ser Val Ser Ser Phe Ser
                420                 425                 430

Ser Arg Thr Met Asn Ala Ser Leu Ala Gln Gln Leu Cys Arg Gln His
            435                 440                 445

Ile Ile Ala Gly Gln His Ile Leu Glu Asp Thr Arg Thr Gln Gln Thr
        450                 455                 460

Arg Arg Trp Trp Thr Leu Ala Gly Gln Glu Ile Thr Val Thr Phe Asn
465                 470                 475                 480

Gln Phe Thr Lys Tyr Ser Tyr Lys Tyr Lys Asp Gln Pro Gln Gln Thr
                485                 490                 495

Phe Asn Ile Tyr Lys Ala Asn Asn Ile Ala Ala Asn Gly Val Phe His
                500                 505                 510

Val Val Thr Gly Leu Arg Trp Gln Ala Pro Ser Gly Thr Pro Gly Asp
            515                 520                 525

Pro Lys Arg Thr Ile Gly Gln Ile Leu Ala Ser Thr Glu Ala Phe Ser
530                 535                 540

Arg Phe Glu Thr Ile Leu Glu Asn Cys Gly Leu Pro Ser Ile Leu Asp
545                 550                 555                 560

Gly Pro Gly Pro Phe Thr Val Phe Ala Pro Ser Asn Glu Ala Val Asp
                565                 570                 575

Ser Leu Arg Asp Gly Arg Leu Ile Tyr Leu Phe Thr Ala Gly Leu Ser
                580                 585                 590

Lys Leu Gln Glu Leu Val Arg Tyr His Ile Tyr Asn His Gly Gln Leu
            595                 600                 605

Thr Val Glu Lys Leu Ile Ser Lys Gly Arg Ile Leu Thr Met Ala Asn
        610                 615                 620

Gln Val Leu Ala Val Asn Ile Ser Glu Glu Gly Arg Ile Leu Leu Gly
625                 630                 635                 640

Pro Glu Gly Val Pro Leu Gln Arg Val Asp Val Met Ala Ala Asn Gly
                645                 650                 655

Val Ile His Met Leu Asp Gly Ile Leu Leu Pro Pro Thr Ile Leu Pro
                660                 665                 670

Ile Leu Pro Lys His Cys Ser Glu Glu Gln His Lys Ile Val Ala Gly
            675                 680                 685

Ser Cys Val Asp Cys Gln Ala Leu Asn Thr Ser Thr Cys Pro Pro Asn
        690                 695                 700

Ser Val Lys Leu Asp Ile Phe Pro Lys Glu Cys Val Tyr Ile His Asp
705                 710                 715                 720

Pro Thr Gly Leu Asn Val Leu Lys Lys Gly Cys Ala Ser Tyr Cys Asn
                725                 730                 735

Gln Thr Ile Met Glu Gly Cys Cys Lys Gly Phe Phe Gly Pro Asp
                740                 745                 750

Cys Thr Gln Cys Pro Gly Gly Phe Ser Asn Pro Cys Tyr Gly Lys Gly
            755                 760                 765

Asn Cys Ser Asp Gly Ile Gln Gly Asn Gly Ala Cys Leu Cys Phe Pro
        770                 775                 780
```

-continued

Asp Tyr Lys Gly Ile Ala Cys His Ile Cys Ser Asn Pro Asn Lys His
785                 790                 795                 800

Gly Glu Gln Cys Gln Glu Asp Cys Gly Cys Val His Gly Leu Cys Asp
            805                 810                 815

Asn Arg Pro Gly Ser Gly Gly Val Cys Gln Gln Gly Thr Cys Ala Pro
            820                 825                 830

Gly Phe Ser Gly Arg Phe Cys Asn Glu Ser Met Gly Asp Cys Gly Pro
            835                 840                 845

Thr Gly Leu Ala Gln His Cys His Leu His Ala Arg Cys Val Ser Gln
            850                 855                 860

Glu Gly Val Ala Arg Cys Arg Cys Leu Asp Gly Phe Glu Gly Asp Gly
865                 870                 875                 880

Phe Ser Cys Thr Pro Ser Asn Pro Cys Ser His Pro Asp Arg Gly Gly
            885                 890                 895

Cys Ser Glu Asn Ala Glu Cys Val Pro Gly Ser Leu Gly Thr His His
            900                 905                 910

Cys Thr Cys His Lys Gly Trp Ser Gly Asp Gly Arg Val Cys Val Ala
            915                 920                 925

Ile Asp Glu Cys Glu Leu Asp Met Arg Gly Gly Cys His Thr Asp Ala
930                 935                 940

Leu Cys Ser Tyr Val Gly Pro Gly Gln Ser Arg Cys Thr Cys Lys Leu
945                 950                 955                 960

Gly Phe Ala Gly Asp Gly Tyr Gln Cys Ser Pro Ile Asp Pro Cys Arg
            965                 970                 975

Ala Gly Asn Gly Gly Cys His Gly Leu Ala Thr Cys Arg Ala Val Gly
            980                 985                 990

Gly Gly Gln Arg Val Cys Thr Cys Pro Pro Gly Phe Gly Gly Asp Gly
            995                 1000                1005

Phe Ser Cys Tyr Gly Asp Ile Phe Arg Glu Leu Glu Ala Asn Ala
            1010                1015                1020

His Phe Ser Ile Phe Tyr Gln Trp Leu Lys Ser Ala Gly Ile Thr
            1025                1030                1035

Leu Pro Ala Asp Arg Arg Val Thr Ala Leu Val Pro Ser
            1040                1045                1050

<210> SEQ ID NO 32
<211> LENGTH: 366
<212> TYPE: DNA
<213> ORGANISM: Artificial sequence
<220> FEATURE:
<223> OTHER INFORMATION: Heavy Chain
<220> FEATURE:
<221> NAME/KEY: CDS
<222> LOCATION: (1)..(366)

<400> SEQUENCE: 32 cag gtt act ctg aaa gag tct ggc cct ggg ata ttg cag ccc tcc cag        48
Gln Val Thr Leu Lys Glu Ser Gly Pro Gly Ile Leu Gln Pro Ser Gln
1               5                   10                  15 acc ctc agt ctg act tgt tct ttc tct ggg ttt tca ctg aac act tct        96
Thr Leu Ser Leu Thr Cys Ser Phe Ser Gly Phe Ser Leu Asn Thr Ser
            20                  25                  30 ggt atg ggt ata ggc tgg att cgt cag cct tca ggg aag ggt ctg gag       144
Gly Met Gly Ile Gly Trp Ile Arg Gln Pro Ser Gly Lys Gly Leu Glu
        35                  40                  45 tgg ctg gca cac att tgg tgg gat gat gac aag cgc tat aac cca gcc       192
Trp Leu Ala His Ile Trp Trp Asp Asp Asp Lys Arg Tyr Asn Pro Ala

```
ctg aag agc cga ctg aca atc tcc aag gat acc tcc agc aac cag gta      240
Leu Lys Ser Arg Leu Thr Ile Ser Lys Asp Thr Ser Ser Asn Gln Val
 65                  70                  75                  80 ttc ctc aag atc gcc agt gtg gac act gca gat act gcc aca tac tac      288
Phe Leu Lys Ile Ala Ser Val Asp Thr Ala Asp Thr Ala Thr Tyr Tyr
                 85                  90                  95 tgt gct cgc cac tat ggt tac gac ccc tac tat gct atg gac tac tgg      336
Cys Ala Arg His Tyr Gly Tyr Asp Pro Tyr Tyr Ala Met Asp Tyr Trp
            100                 105                 110 ggt caa gga acc tca gtc acc gtc tcc tca                              366
Gly Gln Gly Thr Ser Val Thr Val Ser Ser
        115                 120
```

<210> SEQ ID NO 33
<211> LENGTH: 122
<212> TYPE: PRT
<213> ORGANISM: Artificial sequence
<220> FEATURE:
<223> OTHER INFORMATION: Heavy Chain

<400> SEQUENCE: 33

```
Gln Val Thr Leu Lys Glu Ser Gly Pro Gly Ile Leu Gln Pro Ser Gln
  1               5                  10                  15

Thr Leu Ser Leu Thr Cys Ser Phe Ser Gly Phe Ser Leu Asn Thr Ser
             20                  25                  30

Gly Met Gly Ile Gly Trp Ile Arg Gln Pro Ser Gly Lys Gly Leu Glu
         35                  40                  45

Trp Leu Ala His Ile Trp Trp Asp Asp Asp Lys Arg Tyr Asn Pro Ala
 50                  55                  60

Leu Lys Ser Arg Leu Thr Ile Ser Lys Asp Thr Ser Ser Asn Gln Val
 65                  70                  75                  80

Phe Leu Lys Ile Ala Ser Val Asp Thr Ala Asp Thr Ala Thr Tyr Tyr
                 85                  90                  95

Cys Ala Arg His Tyr Gly Tyr Asp Pro Tyr Tyr Ala Met Asp Tyr Trp
            100                 105                 110

Gly Gln Gly Thr Ser Val Thr Val Ser Ser
        115                 120
```

<210> SEQ ID NO 34
<211> LENGTH: 324
<212> TYPE: DNA
<213> ORGANISM: Artificial sequence
<220> FEATURE:
<223> OTHER INFORMATION: Light Chain
<220> FEATURE:
<221> NAME/KEY: CDS
<222> LOCATION: (1)..(324)

<400> SEQUENCE: 34

```
caa att gtt ctc acc cag tct cca gca atc atg tct gca tct cta ggg       48
Gln Ile Val Leu Thr Gln Ser Pro Ala Ile Met Ser Ala Ser Leu Gly
  1               5                  10                  15 gaa cgg gtc acc atg acc tgc act gcc agc tca agt gta agt tcc agt       96
Glu Arg Val Thr Met Thr Cys Thr Ala Ser Ser Ser Val Ser Ser Ser
             20                  25                  30 tat ttg cac tgg tac cag cag agg cca gga tcc tcc ccc aaa ctc tgc      144
Tyr Leu His Trp Tyr Gln Gln Arg Pro Gly Ser Ser Pro Lys Leu Cys
         35                  40                  45 att tat aga aca tcc aac ctg gct tct gga gtc cca cct cgc ttc agt      192
Ile Tyr Arg Thr Ser Asn Leu Ala Ser Gly Val Pro Pro Arg Phe Ser
```

```
           50                  55                  60
ggc agt ggg tct ggg acc tct tac tct ctc aca atc agc agc atg gag    240
Gly Ser Gly Ser Gly Thr Ser Tyr Ser Leu Thr Ile Ser Ser Met Glu
65                  70                  75                  80 gct gaa gat gct gcc act tat tac tgc cac cag tat cat cgt tcc cca    288
Ala Glu Asp Ala Ala Thr Tyr Tyr Cys His Gln Tyr His Arg Ser Pro
                85                  90                  95 ccg acg ttc ggt gga ggc acc aag ctg gaa atc aac                    324
Pro Thr Phe Gly Gly Gly Thr Lys Leu Glu Ile Asn
            100                 105

<210> SEQ ID NO 35
<211> LENGTH: 108
<212> TYPE: PRT
<213> ORGANISM: Artificial sequence
<220> FEATURE:
<223> OTHER INFORMATION: Light Chain

<400> SEQUENCE: 35

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
                20                  25                  30

Tyr Leu His Trp Tyr Gln Gln Arg Pro Gly Ser Ser Pro Lys Leu Cys
            35                  40                  45

Ile Tyr Arg Thr Ser Asn Leu Ala Ser Gly Val Pro Pro Arg Phe Ser
        50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Pro Thr Phe Gly Gly Gly Thr Lys Leu Glu Ile Asn
            100                 105
```

US 12,371,486 B2

HUMANIZED ANTI CLEVER-1 ANTIBODIES AND THEIR USE

CROSS-REFERENCE TO RELATED APPLICATIONS

The present application is a Divisional of U.S. Ser. No. 16/093,257 filed Oct. 12, 2018, which is a National Stage filing under 35 U.S.C. § 371 of PCT/FI2017/050285, filed Apr. 18, 2017, which in turn claims priority to Finnish Patent Application Nos. 20165335, filed Apr. 18, 2016, and 20165336, filed Apr. 18, 2016, each of which are incorporated herein by reference.

FIELD OF THE INVENTION

This invention relates to agents specific for CLEVER-1 protein by recognizing a specific CLEVER-1 epitope and uses thereof.

BACKGROUND OF THE INVENTION

The publications and other materials used herein to illuminate the background of the invention, and in particular, cases to provide additional details respecting the practice, are incorporated by reference.

CLEVER-1 is a protein disclosed in WO 03/057130, Common Lymphatic Endothelial and Vascular Endothelial Receptor-1. It is a binding protein that mediates adhesion of lymphocytes to endothelium in both the systemic vasculature and in the lymphatics. By blocking the interaction of CLEVER-1 and its lymphocyte substrate it is possible to simultaneously control lymphocyte recirculation and lymphocyte migration, and related conditions such as inflammation, at the site of lymphocyte influx into, and efflux from, the tissues. WO 03/057130 further discloses that CLEVER-1 mediates binding of other types of leukocytes such as monocytes and granulocytes to HEV-like vessels. Thus, by blocking the interaction of CLEVER-1 and malignant tumour cells it became possible to control metastasis by preventing malignant cells that bind to CLEVER-1 from being taken up by the lymphatic vessels, and thus to prevent spread of the malignancy into the lymph nodes.

CLEVER-1, i.e. Stabilin-1, has been reviewed by Kzhyshkowska J. (2010), *TheScientificWorldJOURNAL* 10, 2039-2053. Suppression of Th1 Lymphocytes by CLEVER-1 has been recently disclosed by Palani et al. (2016), Journal of Immunology 196: 115-123.

WO 2010/122217 discloses a subtype of macrophages in tumours, in the placenta, and in the blood of pregnant women. The subtype of macrophages is defined as a CLEVER-1 positive macrophage and proposed as type 3 macrophage. By modulating, i.e. counteracting or stimulating, respectively, the CLEVER-1 receptor in this cell the immune system in an individual can be affected. Counteracting or down-regulation of the receptor reduces the size of malignant tumour and/or malignant tumour growth. Stimulating or upregulating the receptor is useful in generation of fetomaternal tolerance and for prevention of pregnancy complications.

The mechanisms of tumour-associated macrophages (TAMs) is also disclosed in the publication by Noy R. and Pollard J. W., "Tumour-Associated Macrophages: From Mechanisms to Therapy", published in Immunity 41, Jul. 17, 2014, p. 49-61. M2 macrophages predominate in human cancers and stimulate tumour growth, but these tumour promoting macrophages can be modulated into tumour growth-inhibiting macrophages, called also as M1 macrophages or pro-inflammatory macrophages, aiming to slow or stop cancer growth. However, it has been noticed that the attempts to treat cancers with the currently available therapeutics aiming at targeting TAMs were accompanied by undesired side effects, e.g. the macrophage therapeutic approaches may have systemic toxicities or paradoxically promote tumour growth, as they target all macrophages.

Particularly preferred CLEVER-1 antagonist monoclonal antibodies 3-266 (DSM ACC2519) and 3-372 (DSM ACC2520), both deposited under the terms of the Budapest Treaty on the International Recognition of the Deposit of Micro-organisms for the Purposes of Patent Procedure on Aug. 21, 2001, with DSMZ-Deutsche Sammlung von Mikroorganismen und Zellkulturen GmbH, Mascheroder Weg 1 b, D-38124 Braunschweig, are disclosed in WO 03/057130.

OBJECT AND SUMMARY OF THE INVENTION

One object of the present invention is to provide an agent capable of binding to a specific epitope of human CLEVER-1. Especially, it has been found out that an agent capable of binding to a specific epitope of human CLEVER-1 can be used to activate macrophages to switch their phenotype from M2 macrophages into M1 macrophages.

Further, an object of the invention is to provide a humanized antibody or humanized single chain Fv or Fab fragment for binding to human CLEVER-1 with an increased binding activity in comparison of monoclonal antibody 3-372 (DSM ACC2520 deposited at DSMZ-Deutsche Sammlung von Mikroorganismen und Zellkulturen GmbH on Aug. 21, 2001).

Therefore, the present invention provides an agent capable of binding to an epitope of human CLEVER-1, wherein the epitope is discontinuous and comprises the sequences:

```
                                    (SEQ ID NO: 1)
PFTVLVPSVSSFSSR,
and (SEQ ID NO: 2)
QEITVTFNQFTK.
```

Especially, the present invention provides an agent capable of binding to human CLEVER-1 recognizing an epitope of CLEVER-1, wherein the epitope is discontinuous and comprises the sequences:

```
                                    (SEQ ID NO: 1)
PFTVLVPSVSSFSSR,
and (SEQ ID NO: 2)
QEITVTFNQFTK,
``` and the agent comprises sequences of complementarity determining regions (CDRs) binding to said epitope sequences selected from the group consisting of

```
                                    (SEQ ID NO: 7)
TSGMGIG, (SEQ ID NO: 8)
HIWWDDDKRYNPALKS,
```

-continued

HYGYDPYYAMDY, (SEQ ID NO: 9)

TASSSVSSSYLH, (SEQ ID NO: 10)

RTSNLAS, (SEQ ID NO: 11)
and

HQYHRSPPT. (SEQ ID NO: 12)

According to the invention, an agent capable of binding to human CLEVER-1 recognizing an epitope of CLEVER-1 defined in the present application may be selected from the group consisting of an antibody, single chain Fv or Fab fragment(s), peptide(s) or any other macromolecule having an adequate affinity to bind to said epitope.

In one aspect the present invention provides an agent capable of binding to human CLEVER-1 in an individual for use in removing tumour or antigen induced immunosuppression by modulating M2 macrophages into M1 macrophages, wherein the agent binds to an epitope of human CLEVER-1, which epitope is discontinuous and comprises the sequences:

PFTVLVPSVSSFSSR, (SEQ ID NO: 1)
and

QEITVTFNQFTK. (SEQ ID NO: 2)

An agent according to the invention capable of binding to human CLEVER-1 on TAMs, preferably to specific epitope sequences on CLEVER-1, is suitable for use in treating or preventing cancer by reducing size of malignant tumour; by reducing malignant tumour growth in an individual; and/or by inhibiting cancer cell transmigration and metastasis formation, wherein immune suppression around the malignant growth is removed by modulating M2 macrophages into M1 macrophages.

An agent according to the invention capable of binding to human CLEVER-1, preferably to specific epitope sequences on CLEVER-1, is also suitable for use in treating chronic infections in an individual, wherein immune suppression against the infective antigens is removed by modulating M2 macrophages into M1 macrophages.

An agent according to the invention capable of binding to human CLEVER-1, preferably to specific epitope sequences on CLEVER-1, is also suitable for use as an adjuvant of a vaccine, wherein immune suppression against vaccine antigens is removed by modulating M2 macrophages into M1 macrophages.

In another aspect, the invention provides a humanized antibody or single chain Fv or Fab fragment capable of binding to an epitope of human CLEVER-1, wherein the epitope is discontinuous and comprises the sequences:

PFTVLVPSVSSFSSR, (SEQ ID NO: 1)
and

QEITVTFNQFTK, (SEQ ID NO: 2)

and said antibody or single chain Fv or Fab fragment comprises
a) constant regions of human IgG4 heavy chain and kappa light chain, and
b) one or more of the following sequences of complementarity determining regions (CDRs)

i) of the heavy chain
CDR 1:
TSGMGIG, (SEQ ID NO: 7)
and/or

CDR 2:
HIWWDDDKRYNPALKS, (SEQ ID NO: 8)
and/or

CDR 3:
HYGYDPYYAMDY; (SEQ ID NO: 9)
and ii) of the light chain
CDR 1:
TASSSVSSSYLH, (SEQ ID NO: 10)
and/or CDR 2:
RTSNLAS, (SEQ ID NO: 11)
and/or

CDR 3:
HQYHRSPPT. (SEQ ID NO: 12)

Another object of the present invention is also to provide a pharmaceutical composition comprising the agent capable of binding to human CLEVER-1 or the humanized antibody or the single chain Fv or Fab fragment according to the invention and an appropriate excipient.

The present invention also provides a pharmaceutical composition comprising the agent capable of binding to human CLEVER-1 or the humanized antibody or the single chain Fv or Fab fragment as defined above and an appropriate excipient for use in removing tumour or antigen induced immunosuppression.

A pharmaceutical composition according to the invention is suitable for use in treating or preventing cancer by reducing size of malignant tumour; by reducing malignant tumour growth in an individual; and/or by inhibiting cancer cell transmigration and metastasis formation. A pharmaceutical composition according to the invention is also suitable for use treatment of chronic infections in an individual or for use as an adjuvant of a vaccine.

DETAILED DESCRIPTION OF THE INVENTION

Terms

Figure 1A:
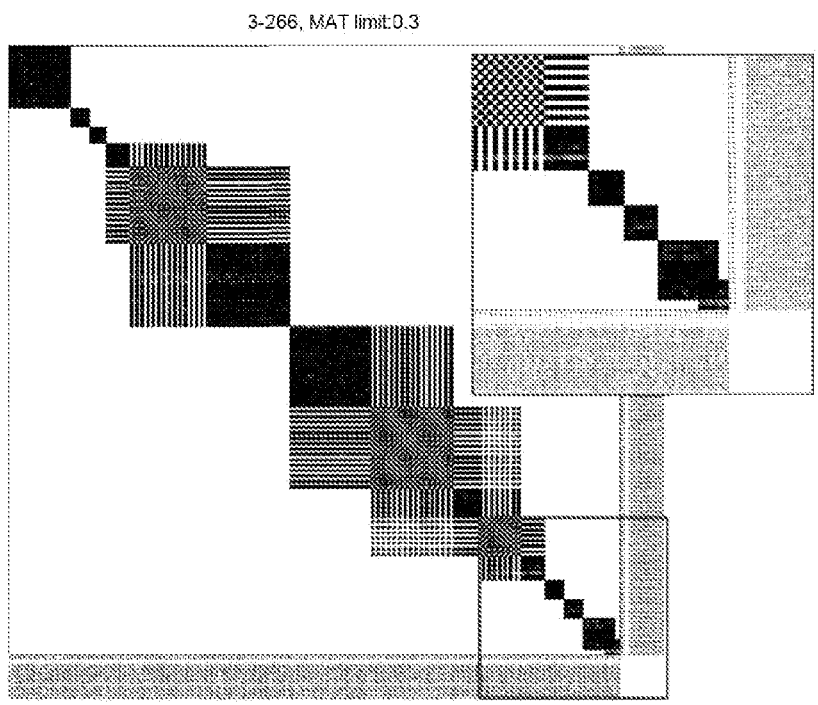
FIGS. 1a and 1b illustrate heatmap representation of results obtained for antibody 3-266 and antibody AK FUMM 9-11.

The term "an agent capable of binding to an epitope of human CLEVER-1" refers to agents including antibodies and fragments thereof, peptides or the like, which are capable of binding to specific epitope sequences defined in the present application. The agent may also be any other macromolecule having an adequate affinity to bind to said epitope.

The term "an antibody or a fragment thereof" is used in the broadest sense to cover an antibody or a fragment thereof which are capable to bind CLEVER-1 molecule in an individual. Especially, it shall be understood to include chimeric, humanized or primatized antibodies, as well as antibody fragments and single chain antibodies (e.g. Fab, Fv), so long they exhibit the desired biological activities.

The term humanized antibody refers to any antibody wherein the constant regions of non-human antibodies have been fully substituted with the human form of the constant regions, and at least parts of the variable regions of the non-human antibodies, excluding the three loops of amino acid sequences at the outside of each variable region that bind to the target structure, have been fully or partially substituted with corresponding parts of human antibodies. Thus, in particular, any antibody named by the naming scheme for the World Health Organization's International Nonproprietary Names (INN) or the United States Adopted Names (USAN) for pharmaceuticals with substems -xizu- or -zu- is in this application referred to as a humanized antibody.

The term variable domain, also referred to as the Fv region, is the most important region for binding to antigens. To be specific, variable loops of β-strands, three on each light ($V_L$) and heavy ($V_H$) chain, are responsible for binding to the antigen. These loops are referred to as the complementarity determining regions (CDRs).

The term single-chain Fv fragment or scFv refers to fragments that are obtained by connecting the $V_H$ and the $V_L$ domains by a linker in a single polypeptide. The term humanized single-chain Fv fragment or scFv refers, in analogy with the definition of the term humanized antibody above, to any single-chain Fv fragment or scFv wherein the constant regions originating from non-human antibodies have been fully substituted with the human form of the constant regions, and at least parts of the variable regions originating from non-human antibodies, excluding the three loops of amino acid sequences at the outside of each variable region that bind to the target structure, have been fully or partially substituted with corresponding parts of human antibodies.

The term Fab fragment refers to a region on an antibody that binds to antigens. The term humanized Fab fragment refers, also in analogy with the definition of the term humanized antibody above, to any Fab fragment wherein the constant regions originating from non-human antibodies have been fully substituted with the human form of the constant regions, and at least parts of the variable regions originating from non-human antibodies, excluding the three loops of amino acid sequences at the outside of each variable region that bind to the target structure, have been fully or partially substituted with corresponding parts of human antibodies.

The term "peptide" refers to any peptide which comprises one or more amino acid sequences of complementarity determining regions (CDRs) defined in the present application and which peptide is capable of binding to at least one epitope of human CLEVER-1.

Preferred Embodiments

One embodiment of the present invention is directed to an agent capable of binding to human CLEVER-1 recognizing an epitope of CLEVER-1, wherein the epitope is discontinuous and comprises the amino acid sequences:

```
                                        (SEQ ID NO: 1)
PFTVLVPSVSSFSSR,
and (SEQ ID NO: 2)
QEITVTFNQFTK,
of human CLEVER-1
``` and said agent comprises one or more amino acid sequences of complementarity determining regions (CDRs) binding to said epitope sequences selected from the group consisting of

```
                                        (SEQ ID NO: 7)
TSGMGIG, (SEQ ID NO: 8)
HIWWDDDKRYNPALKS, (SEQ ID NO: 9)
HYGYDPYYAMDY, (SEQ ID NO: 10)
TASSSVSSSYLH, (SEQ ID NO: 11)
RTSNLAS,
and (SEQ ID NO: 12)
HQYHRSPPT.
```

In some preferred embodiments of the present invention the discontinuous epitope of human CLEVER-1 further comprises one or more of amino acid sequences selected from the group consisting of

```
                                     (SEQ ID NO: 3)
          ATQTGRVFLQ, (SEQ ID NO: 4)
          DSLRDGRLIYLF, (SEQ ID NO: 5)
          SKGRILTMANQVL,
          and (SEQ ID NO: 6)
          LCVYQKPGQAFCTCR.
```

A part of the target protein human CLEVER-1, i.e. human Stabilin-1, has defined in SEQ ID NO: 31. The epitopes SEQ ID NO: 1, SEQ ID NO: 2, SEQ ID NO: 3, SEQ ID NO: 4, SEQ ID NO: 5 and SEQ ID NO: 6 on the CLEVER-1 corresponds amino acids 420-434, 473-484, 390-399, 576-587, 615-627 and 313-327 of target protein human CLEVER-1 defined in SEQ ID NO: 31.

In some preferred embodiments of the present invention the agent capable of binding to an epitope of human CLEVER-1 comprises at least two, preferably three, more preferably four, even more preferably five, and most preferably all six amino acid sequences of complementarity determining regions (CDRs) defined above.

According to the present invention, the agent capable of binding to human CLEVER-1 may be selected from the group consisting of an antibody, single chain Fv or Fab fragment(s), peptide(s) or macromolecule(s).

In some preferred embodiments of the present invention an agent capable of binding to human CLEVER-1 is a humanized antibody or single chain Fv or Fab fragment and said antibody or humanized single chain Fv or Fab fragment comprises
  a) constant regions of human IgG heavy chain and kappa light chain, and
  b) one or more of the following sequences of complementarity determining regions (CDRs)

```
          i) of the heavy chain
          CDR 1:
                                     (SEQ ID NO: 7)
          TSGMGIG,
          and/or CDR 2:
                                     (SEQ ID NO: 8)
          HIWWDDDKRYNPALKS,
          and/or CDR 3:
                                     (SEQ ID NO: 9)
          HYGYDPYYAMDY;
          and ii) of the light chain
          CDR 1:
                                     (SEQ ID NO: 10)
          TASSSVSSSYLH,
          and/or CDR 2:
                                     (SEQ ID NO: 11)
          RTSNLAS,
          and/or
```

-continued
```
          CDR 3:
                                     (SEQ ID NO: 12)
          HQYHRSPPT.
```

The humanized antibody or single chain Fv or Fab fragment capable of binding to an epitope of human CLEVER-1 recognizing discontinuous epitope sequences as defined above. The discontinuous epitope of human CLEVER-1 comprises at least sequences SEQ ID NO: 1 and SEQ ID NO: 2. In some embodiments the discontinuous epitope of human CLEVER-1 further comprises one or more of sequences selected from the group consisting of SEQ ID NO: 3, SEQ ID NO: 4, SEQ ID NO: 5, and SEQ ID NO: 6.

In some embodiments of the present invention referred to above at least two, preferably three, more preferably four, even more preferably five, and most preferably all six CDRs defined above are comprised in the humanized antibody or single chain Fv or Fab fragment.

In some embodiments of the present invention the human IgG heavy chain variable region sequence of the humanized antibody or single chain Fv or Fab fragment is selected from the group consisting of SEQ ID NO: 14, SEQ ID NO: 16, SEQ ID NO 18: and SEQ ID NO: 20, preferably SEQ ID NO: 16, SEQ ID NO: 18 and SEQ ID NO: 20. In some embodiments of the present invention the human IgG light chain variable region sequence of the humanized antibody or single chain Fv or Fab fragment is selected from the group consisting of SEQ ID NO: 22, SEQ ID NO: 24, SEQ ID NO: 26, SEQ ID NO: 28 and SEQ ID NO: 30, preferably SEQ ID NO: 30.

In many embodiments of the humanized antibody or single chain Fv or Fab fragment according to the invention the constant regions of the human IgG heavy chain and kappa light chain are as such. Human IgG4 constant regions are preferred. Many preferred embodiments comprise the human IgG4 heavy and IgG4 kappa light chain with mutations L248E and/or, preferably and, S241P.

In some embodiments of the present invention the humanized antibody or the single chain Fv or Fab fragment is capable of binding to human CLEVER-1 with a relative IC50<1.0, preferably <0.8, more preferably <0.6 and most preferably <0.5 in comparison to the IC50 of monoclonal antibody 3-372 (DSM ACC2520 deposited at DSMZ-Deutsche Sammlung von Mikroorganismen und Zellkulturen GmbH on Aug. 21, 2001).

According to one embodiment of the invention the combination of the human IgG heavy and light chain variable regions are selected from the combinations presented in Table 5 having capable of binding to human CLEVER-1 with a relative IC50<1.0 in comparison to the IC50 of monoclonal antibody 3-372 (DSM ACC2520 deposited at DSMZ-Deutsche Sammlung von Mikroorganismen und Zellkulturen GmbH on Aug. 21, 2001).

A pharmaceutical composition according to the invention comprises the agent capable of binding to human CLEVER-1 or the humanized antibody or the single chain Fv or Fab fragment described above and an appropriate excipient.

A Modulation of Tumour Promoting Macrophages (M2) into Pro-Inflammatory Macrophages (M1)

It has also been found out that an agent capable of binding to human CLEVER-1, especially to specific epitope sequences on CLEVER-1 defined in the present application, can be used to activate macrophages to switch their phenotype from M2 macrophages into M1 macrophages. Especially, an agent capable of binding to CLEVER-1 on TAMs can be used to achieve a modulation of tumour promoting macrophages (M2) into pro-inflammatory macrophages (M1). This modulation increases T-cell activation and eventually leads e.g. to removal of cancer originated immune suppression. More precisely, it has been found out that an agent capable of binding to specific sequences on CLEVER-1 molecule can be used to remove immune suppression by modulating M2 macrophages into M1 macrophages. Consequently, the present finding provides a method for affecting the immune system in an individual and is especially useful in treating cancer or preventing metastasis, but not limited to this approach.

Macrophages may be divided into two distinct phenotypes: M1 and M2 macrophages. M1 macrophages are classical pro-inflammatory macrophages, which produce large quantities of pro-inflammatory cytokines and co-stimulatory molecules, and are very efficient in activation of T-cell responses. M2 macrophages, in contrast, are immune suppressing cells, which synthesize anti-inflammatory cytokines and induce regulatory T cells and hence profoundly dampen antigen-driven T cell activation. Tumour-associated macrophages (TAMs) are considered harmful as they mature into M2 macrophages (tumour promoting macrophages) within the tumour environment and suppress anti-tumour immune response and mediate angiogenic switch, a crucial step in cancer growth. The M2 macrophages can be modulated into M1 macrophages (pro-inflammatory macrophages) and such phenotype conversion from M2 to M1 may directly or indirectly cause tumour rejection.

In the present context the expression "M1 macrophages" or "pro-inflammatory macrophages" refers to the macrophages characterized by an increased measured level of macrophage/monocyte TNF-alpha (TNF-$\alpha$) secretion or HLA-DR expression. The modulation of M2 macrophages into M1 macrophages will increase monocyte TNF-alpha secretion and also HLA-DR expression compared to the control values measured before administering an agent capable of binding to human CLEVER-1 or the values of one or more previous measurements carried out at different time points in the same patient. It is important to compare measured values of monocyte TNF-alpha secretion and HLA-DR expression to the values of the same patient, since the level of these markers may vary from an individual to another and e.g. cytokines such as interferon-gamma and LPS activation may increase TNF-alpha expression by the M2 macrophages.

It has surprisingly been found that M2 macrophages can be activated to modulate M1 macrophages by contacting the said macrophages by an agent capable of binding to human CLEVER-1, e.g. by an antibody or a fragment thereof, peptide(s) or macromolecule(s) as defined in the present application. Especially it has been found out that the M2 macrophages associated with malignant tumours can be modulated or re-polarized into M1 macrophages by contacting the said macrophages by an agent capable of binding to human CLEVER-1 on TAMs. Both phenotypes may be present at same time and both of the phenotypes may be found in tumours.

An agent capable of binding to human CLEVER-1, such as an antigen or a fragment thereof, peptide(s) or macromolecule(s), is bound to human CLEVER-1 for achieving said modulation or re-polarization of macrophage phenotypes. It has been identified that the agents specific for CLEVER-1 protein recognize a specific CLEVER-1 epitope sequences defined in the present application.

A specific binding to two or more said epitope sequences on CLEVER-1 on TAMs will provide a novel method for treating cancers or preventing metastasis without harmful side-effects since the treatment can be targeted to specific epitopes for achieving desired modulation of macrophage phenotype. Consequently, the findings described here are especially useful in the treatment or prevention of all kinds of malignant tumours associated with an increased amount of tumour promoting macrophages or other pathologies such as chronic inflammation where an individual presents a dominance of immune suppression. Consequently, a method for treating cancer or preventing metastasis comprising administering to an individual an agent capable of binding to human CLEVER-1, preferably to specific epitopes on CLEVER-1 molecule defined above. The method comprises treating or preventing cancer by reducing tumour size and/or; by reducing tumour growth in an individual; and/or by inhibiting cancer cell transmigration and metastasis formation. Thus, any benign or malignant tumour or metastasis of malignant tumour, such as skin cancer and colon cancer can be treated. Also leukemias, lymphomas and multiple myelomas can be treated. Particularly, melanomas and lymphomas are expected to respond very well to the treatment based on animal models.

Macrophages have also an important role during inflammation and infection resolution besides affecting in the growth or regression of tumours. In infections, a switch from M1 to M2 macrophage can occur, leading to the generation of suppressive environment that abrogates effector immunity. Consequently, the findings described here to modulate macrophages phenotype are also useful in the treatment of chronic infections to remove immune suppression against the infective antigens. The invention also concerns a method for treating chronic infections comprising administering to an individual an agent capable of binding to CLEVER-1, preferably to two or more specific epitope sequences on CLEVER-1 molecule defined in the present application, wherein said agent may activate macrophages to switch their phenotype from M2 into M1.

Further, an agent capable of binding to CLEVER-1 molecule on macrophages and monocytes in an individual can be used as an adjuvant in vaccines. The said agent achieves re-polarization of macrophages and thus removes or at least decreases immune suppression against the vaccine antigens. Any antigen-induced vaccination may benefit if the host or vaccination site can temporally be removed from immune suppressive elements.

The modulation of M2 into M1 macrophages may be verified by measuring monocyte TNF-alpha secretion from human blood samples. Consequently, the increased secretion of TNF-alpha may be used as a marker for monitoring treatment response in an individual. The TNF-alpha secretion may be determined from the peripheral blood monocytes enriched from the blood drawn from a patient. A level of the TNF-alpha measured may be used as a marker for the patient response to the treatment comprising administering an agent capable of binding to CLEVER-1 in the patient, when the level is compared to control level measured from the same patient before administering said agent in the patient, or the values of one or more previous measurements carried out at different time points in the same patient.

A method for estimating of the efficacy of anti-CLEVER-1 therapy by monitoring a development of a modulation of M2 macrophages into M1 macrophages, when an agent capable of binding to CLEVER-1, preferably to said one two or more specific epitope sequences on CLEVER-1, is administered in a patient, comprising the steps of
  (a) obtaining peripheral blood monocytes (PBLs) from a blood sample drawn from said patient,
  (b) measuring the TNF-α secretion of said PBLs, and/or
  (c) measuring HLA-DR expression on CD14 positive PBLs, and
  (e) comparing values of the TNF-α secretion and/or the HLA-DR expression measured in steps (b) and (c) to control values for an estimation of the efficacy of the anti-CLEVER-1 treatment, wherein the control values are the values measured before administering an agent capable of binding to CLEVER-1 in the patient or the values of one or more previous measurements carried out at different time points in the same patient and wherein an increased TNF-alpha secretion or HLA-DR expression is indicative of modulation of M2 macrophages into M1 macrophages.

Determining of TNF-alpha secretion from peripheral blood monocytes obtained from a blood sample drawn from the patient can be carried commonly known methods, for example by using a commercial TNF-alpha ELISA kit. The HLA-DR expression on CD14 positive monocytes can also be monitored by using a known method by flow cytometry.

The development of modulation of M2 macrophages into M1 macrophages may be monitored by comparing a measured level of monocyte TNF-alpha secretion to the control values measured before administering an agent capable of binding to CLEVER-1 in the patient, or the values of one or more previous measurements carried out at different time points in the same patient. For example, a decreased level of monocyte TNF-alpha secretion compared to the results from previous measurements or to a control may be used to indicate higher expression of M2 macrophages, while an increased level of TNF-alpha, compared to the results from previous measurements or to a control may be used to indicate that more expression of M1 macrophages with lower expression of M2 macrophages, wherein it can also be used to indicate the efficacy of the anti-CLEVER-1 treatment. The increased level of TNF-alpha indicates more expression of M1 macrophages with lower expression of M2 macrophages, i.e. it attributes responsiveness to said therapy. An agent capable of binding to CLEVER-1 will activate at least a part of the M2 macrophages to re-polarize into M1 macrophages and after the administration of said agent both macrophage phenotypes may be present, but the increased expression of the M1 macrophages may be observed compared to the situation before the administration of said agent. Typically, at least a two fold increase of the measured TNF-alpha secretion compared to the control value is indicative of modulation of M2 macrophages into M1 macrophages and so to indicate the patient responsiveness to the therapy.

Diseases Responding to the Treatment

Balancing immune activation and suppression is very critical for the homeostasis of a human (or animal) in fights against foreign material born in or entering the human (or animal). The example of Palani et al. (2016) is a physiological example of this and shows how local immune suppression is critical for the wellbeing of an embryo in an environment dominated by a mother's immune defence. The same could take place in chronic infections as some pathogens (e.g. tuberculosis) have learned to utilize a similar hiding mechanism against the host immune system and could establish chronically infected sites (hepatitis). To remove this local immune suppression could help the host to fight against these infections as it would do to improve vaccination against these resistant pathogens.

Tumours have adapted this immune suppression to their benefit as well. The method according to the present invention for treating or preventing cancer by reducing the size of malignant tumour; by reducing malignant tumour growth; and/or by inhibiting cancer cell transmigration and metastasis formation is applicable to all forms of cancers. Thus, any benign or malignant tumour or metastasis of malignant tumour, such as skin cancer and colon cancer can be treated. Also leukemias, lymphomas and multiple myelomas can be treated. Particularly, melanomas and lymphomas are expected to respond very well to the treatment based on animal models.

We believe that the agent capable of binding to CLEVER-1 or a humanized antibody or single chain Fv or Fab fragment according to the present invention or the pharmaceutical composition according to the present invention is useful in the treatment or prevention of all kinds of sarcomas, for example fibrosarcoma, liposarcoma, chondrosarcoma, osteosarcoma, angiosarcoma, lymphangisarcoma, leiomyosarcoma, and rhabdomyosarcoma, mesothelioma, meningoma, leukemias, lymphomas, as well as all kinds of carcinomas, such as squamous cell carcinomas, basal cell carcinoma, adenocarcinomas, papillary carcinomas, cystadenocarcinomas, bronchogenic carcinomas, melanomas, renal cell carcinomas, hepatocellular carcinoma, transitional cell carcinomas, choriocarcinomas, seminomas, and embryonal carcinomas.

An agent capable of binding to human CLEVER-1 in an individual or a humanized antibody or single chain Fv or Fab fragment or a pharmaceutical composition according to the invention is suitable for use in removing tumour or antigen induced immunosuppression by modulating M2 macrophages into M1 macrophages, wherein the agent binds to an epitope sequences of human CLEVER-1 defined in the present application.

An agent capable of binding to human CLEVER-1 in an individual or a humanized antibody or single chain Fv or Fab fragment or a pharmaceutical composition according to the invention is suitable for use in treating or preventing cancer by reducing size of malignant tumour; by reducing malignant tumour growth in an individual; and/or by inhibiting cancer cell transmigration and metastasis formation, wherein immune suppression around the malignant growth is removed by modulating M2 macrophages into M1 macrophages.

An agent capable of binding to human CLEVER-1 in an individual or a humanized antibody or single chain Fv or Fab fragment or a pharmaceutical composition according to the invention is also suitable for use in treating chronic infections in an individual, wherein immune suppression against the infective antigens is removed by modulating M2 macrophages into M1 macrophages.

An agent capable of binding to human CLEVER-1 in an individual or a humanized antibody or single chain Fv or Fab fragment or a pharmaceutical composition according to the invention is also suitable for use as an adjuvant of a vaccine, wherein immune suppression against vaccine antigens is removed by modulating M2 macrophages into M1 macrophages.

A method for modulating M2 macrophages into M1 macrophages comprises administering to a subject in need thereof an agent capable of binding to CLEVER-1, preferably capable of binding to specific sequences on CLEVER-1 molecule as defined in the present application. The said method can be used in treatment of cancer or in preventing metastasis in an individual, or in treatment of chronic infections in an individual. The treatment response may be verified by measuring the TNF-α secretion of said PBLs and/or HLA-DR expression on CD14 positive PBLs as described on the present application.

Administration Routes, Formulations and Required Dose

The pharmaceutical compositions to be used in the present invention can be administered by any means that achieve their intended purpose. For example, administration can be intravenous, intraarticular, intra-tumoural or subcutaneous. In addition to the pharmacologically active compounds, the pharmaceutical preparations of the compounds preferably contain suitable pharmaceutically acceptable carriers comprising excipients and auxiliaries that facilitate processing of the active compounds into preparations that can be used pharmaceutically.

The dose chosen should be therapeutically effective with regard to the disease treated. Accordingly immunosuppression should be sufficient to treat the disease without effects essentially endangering the sought outcome of the treatment. When treating or preventing cancer the dose should be sufficient to reduce size of malignant tumour, reduce malignant tumour growth and/or inhibit cancer cell transmigration and metastasis formation. The dose is dependent on the turnover of the administered agent but typically these treatments follow a regimen of 1 to 5 mg/kg every other 2 to 4 weeks.

EXAMPLES

The following experimental section illustrates the invention by providing examples.

The examples 1 to 10 illustrate discontinuous epitope mapping of human CLEVER-1 and generation of humanized antibodies from the 3-372 mouse monoclonal antibody (DSM ACC2520 deposited at DSMZ-Deutsche Sammlung von Mikroorganismen and Zellkulturen GmbH on Aug. 21, 2001) using Composite Human Antibody™ technology. Anti-CLEVER-1 antibodies ability to promote immune activation is illustrated in Examples 11 to 14.

Example 1 illustrates full discontinuous epitope mapping of antibodies, which target human CLEVER-1.

Examples 2 to 6 illustrate determination of heavy and light chain V region ($V_H$ and $V_K$) sequences of the anti-Clever 1 antibody clone 3-372 and production of chimeric antibodies comprising 3-372 variable regions and human IgG4 heavy chain and kappa light chain constant regions. mRNA was extracted from hybridoma clone 3-372, reverse transcribed, PCR amplified and antibody-specific transcripts were cloned. The nucleotide and amino acid sequences of the antibody heavy and light chain variable regions were determined, and an analysis of the sequence data was performed for humanization using Antitope's proprietary Composite Human Antibody™ technology.

Examples 2 to 6 demonstrate that: Variable regions from the 3-372 mouse anti-Clever 1 antibody have been cloned and sequenced. Variable region genes have been combined with human IgG4(S241P) heavy chain and kappa light chain constant regions and expressed in NS0 cells to produce a chimeric anti-Clever 1 antibody. A competition ELISA assay from NS0-derived chimeric antibody was used to demonstrate that the binding efficiency of the chimeric antibody for Clever-1 is similar to that of the parental murine antibody.

Examples 7 to 10 illustrate: Design of anti-CLEVER-1 Composite Human Antibodies™ which were expressed and tested for binding to human Clever-1. Key residues involved in the structure and binding of anti-CLEVER-1 were determined by structure and homology modelling to generate a 'constraining residue map'. The constraining residue map was used as a template to source segments of human V region sequence from databases containing unrelated human antibody sequences. Each selected sequence segment, as well as the junctions between segments, were tested for the presence of potential T cell epitopes using in silico (iTope™ and TCED™) analysis. Using this method, all Composite Human Antibody™ sequence variants were designed to avoid T cell epitopes. Composite Human Antibody™ V region genes were generated using synthetic oligonucleotides encoding combinations of the selected human sequence segments. These were then cloned into vectors containing human IgG4(S241P) heavy chain and kappa light chain constant regions, and antibodies were produced and tested for binding to target antigen by competition ELISA in comparison to the original reference murine monoclonal antibody.

Examples 7 to 10 demonstrate construction of four VH and five $V_\kappa$ Composite Human Antibody™ V regions. Combinations of composite heavy and light chains were expressed in NS0 cells, purified and tested for binding to CLEVER-1 in a competition ELISA assay. The results demonstrated that the binding efficiency of many of the Composite Human Antibodies™ to CLEVER-1 was at least as good as that of the chimeric reference antibody and several were markedly better. Based on the absence of a potential glycosylation site and an unpaired cysteine, and expression and binding efficiency data sets generated, three potential leads were designated as follows: VH2/VK5, VH3/VK5, and VH4/VK5.

Examples 11 to 12 illustrate anti-CLEVER-1 antibody binding on human peripheral blood monocytes and activating TNF-alpha secretion on human peripheral blood monocytes. Example 13 illustrates the mode of action of anti-CLEVER-1-antibodies on tumor-associated macrophages in mouse syngeneic cancer models. Example 14 illustrates that CLEVER-1 ligation with 9-11 and 3-372 antibodies promotes opposing effects on mTOR and c-Jun signaling in human peripheral blood monocytes.

Example 1

Full Discontinuous Epitope Mapping of Human CLEVER-1

Tentative discontinuous epitopes for four antibodies were established employing Pepscan analysis. Antibodies FAR02 VH3/VK5 and FU—HI-3-372 target same discontinuous epitope, while antibodies 3-266 and AK FUMM 9-11 target other distinct epitopes. The study was conducted at Pepscan Presto BV, (Zuidersluisweg 2, 8243RC Lelystad, The Netherlands).

The antibodies 3-266, FAR02 VH3/VK5, FU—HI-3-372 and AK FUMM 9-11 were provided by Faron Pharmaceuticals Oy.

The target protein human CLEVER-1, i.e. human Stabilin-1, was defined by SEQ ID NO: 31. Disulfide bridges connect residues (numbering Uniprot STAB1_HUMAN):

| | | | | | | | | | | | |
|---|---|---|---|---|---|---|---|---|---|---|---|
| 112 | 126 | 120 | 136 | 138 | 147 | 160 | 171 | 164 | 181 | 183 | 192 |
| 199 | 210 | 204 | 217 | 236 | 247 | 241 | 257 | 259 | 270 | 732 | 746 |
| 740 | 756 | 758 | 767 | 822 | 837 | 831 | 846 | 865 | 879 | 873 | 889 |
| 891 | 902 | 908 | 922 | 916 | 932 | 934 | 945 | 951 | 964 | 958 | 974 |

CLIPS Technology

The CLIPS technology employed structurally fixes peptides into defined three-dimensional structures. This results in functional mimics of even the most complex binding sites. CLIPS technology is now routinely used to shape peptide libraries into single, double or triple looped structures as well as sheet- and helix-like folds. The CLIPS reaction takes place between bromo groups of the CLIPS scaffold and thiol sidechains of cysteines. The reaction is fast and specific under mild conditions. Using this elegant chemistry, native protein sequences are transformed into CLIPS constructs with a range of structures. (Timmerman et al., *J. Mol. Recognit.* 2007; 20: 283-29)

CLIPS library screening starts with the conversion of the target protein into a library of up to 10,000 overlapping peptide constructs, using a combinatorial matrix design. On a solid carrier, a matrix of linear peptides is synthesized, which are subsequently shaped into spatially defined CLIPS constructs. Constructs representing both parts of the discontinuous epitope in the correct conformation bind the antibody with high affinity, which is detected and quantified. Constructs presenting the incomplete epitope bind the antibody with lower affinity, whereas constructs not containing the epitope do not bind at all. Affinity information is used in iterative screens to define the sequence and conformation of epitopes in detail. The target protein containing a discontinuous conformational epitope is converted into a matrix library. Combinatorial peptides are synthesized on a proprietary minicard and chemically converted into spatially defined CLIPS constructs.

Heat Map Analysis

A heat map is a graphical representation of data where the values taken by a variable in a two-dimensional map are represented as colors.

For double-looped CLIPS peptides, such a two-dimensional map can be derived from the independent sequences of the first and second loops. For example, sequences of the 16 CLIPS peptides are effectively permutations of e.g. 4 unique sub-sequences in e.g. loop 1 and e.g. 4 unique sub-sequences in e.g. loop 2. Thus, observed ELISA data can be plotted in a 4×4 matrix, where each X coordinate corresponds to the sequence of the first loop, and each Y coordinate corresponds to the sequence of the second loop.

To further facilitate the visualization, ELISA values can be replaced with colours from a continuous gradient. For example extremely low values can be coloured in green, extremely high values in coloured in red, and average values are coloured in black.

Synthesis of Peptides

To reconstruct epitopes of the target molecule a library of peptides was synthesized. An amino functionalized polypropylene support was obtained by grafting with a proprietary hydrophilic polymer formulation, followed by reaction with t-butyloxycarbonyl-hexamethylenediamine (BocHMDA) using dicyclohexylcarbodiimide (DCC) with Nhydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer).

Synthesis of structural mimics was done using Pepscan's proprietary Chemically Linked Peptides on Scaffolds (CLIPS) technology. CLIPS technology allows to structure peptides into single loops, double-loops, triple loops, sheet-like folds, helix-like folds and combinations thereof. CLIPS templates are coupled to cysteine residues. The side-chains of multiple cysteines in the peptides are coupled to one or two CLIPS templates. For example, a 0.5 mM solution of the P2 CLIPS (2,6-bis(bromomethyl)pyridine) is dissolved in ammonium bicarbonate (20 mM, pH 7.8)/acetonitrile (1:3 (v/v)). This solution is added onto the peptide arrays. The CLIPS template will bind to side-chains of two cysteines as present in the solid-phase bound peptides of the peptide-arrays (455 wells plate with 3 µl wells). The peptide arrays are gently shaken in the solution for 30 to 60 minutes while completely covered in solution. Finally, the peptide arrays are washed extensively with excess of $H_2O$ and sonicated in disrupt-buffer containing 1% SDS/0.1 beta-mercaptoethanol in PBS (pH 7.2) at 70° C. for 30 minutes, followed by sonication in $H_2O$ for another 45 minutes. The T3 CLIPS carrying peptides were made in a similar way but now with three cysteines.

ELISA Screening

The binding of antibody to each of the synthesized peptides was tested in a PEPSCAN-based ELISA. The peptide arrays were incubated with primary antibody solution (overnight at 4° C.). After washing, the peptide arrays were incubated with a 1/1000 dilution of an appropriate antibody peroxidase conjugate (SBA; Table 1) for one hour at 25° C. After washing, the peroxidase substrate 2,2'-azino-di-3-ethylbenzthiazoline sulfonate (ABTS) and 20 µl/ml of 3 percent $H_2O_2$ were added. After one hour, the colour development was measured. The colour development was quantified with a charge coupled device (CCD)—camera and an image processing system.

TABLE 1

Details of the antibodies

| Name | Supplier | Cat. No |
| --- | --- | --- |
| goat anti-human HRP conjugate | Southern Biotech | 2010-05 |
| rabbit anti-mouse IgG (J + L) HRP conjugate | Southern Biotech | 6175-05 |
| goat anti-rat IgM + IgG (H + L) HRP conjugate | Southern Biotech | 3010-05 |

Langedijk et al. (2011). Helical peptide arrays for lead identification and interaction site mapping, *Analytical Biochemistry* 417: 149-155

Design of Peptides

Different sets of peptides were synthesized according to the following designs. Note that in some sets peptides were synthesized in a random order. Below the actual peptide order is shown.

| Set 1 | |
| --- | --- |
| Mimic Type | linear |
| Label | LIN |
| Description | Linear 15-mer peptides derived from the target sequence of human Clever-1 with an offset of one residue. |
| Sequences | (first 10)<br>QVLFKGCDVKTTFVT<br>VLFKGCDVKTTFVTH<br>LFKGCDVKTTFVTHV<br>FKGCDVKTTFVTHVP<br>KGCDVKTTFVTHVPC<br>GCDVKTTFVTHVPCT<br>CDVKTTFVTHVPCTS<br>DVKTTFVTHVPCTSC<br>VKTTFVTHVPCTSCA<br>KTTFVTHVPCTSCAA |

| Set 2 | |
|---|---|
| Mimic Type | linear |
| Label | LIN.AA |
| Description | Peptides of set 1, but with residues on positions 10 and 11 replaced by Ala. Once a native Ala would occur on either position, it is replaced by Gly. |
| Sequences | (first 10)<br>GAETPCNGHAACLDG<br>LTMANQVLAAAISEE<br>ILLPPTILPAAPKHC<br>DRNGTCVCQAAFRGS<br>PGYTQQGSEAAAPNP<br>PIDPCRAGNAACHGL<br>HTDALCSYVAAGQSR<br>KGCDVKTTFAAHVPC<br>CQALNTSTCAANSVK<br>RAVGGGQRVAACPPG |

| Set 3 | |
|---|---|
| Mimic Type | linear |
| Label | LIN20.0 |
| Description | Linear peptides of length 20 derived from the target sequence of human Clever-1 with an offset of one residue. Cys residues are protected by acetimidomethyl (Acm, denoted "2"). |
| Sequences | (first 10)<br>2H2PENYHGDGMV2LPKDP2<br>SGWLRELPDQITQD2RYEVQ<br>LAQH2HLHAR2VSQEGVAR2<br>IKKQT2PSGWLRELPDQITQ<br>2RESEVGDGRA2YGHLLHEV<br>QRV2T2PPGFGGDGFS2YGD<br>NGVFHVVTGLRWQAPSGTPG<br>AT2QVTADGKTS2V2RESEV<br>KYSYKYKDQPQQTFNIYKAN<br>2VYIHDPTGLNVLKKG2ASY |

| Set 4 | |
|---|---|
| Mimic Type | linear |
| Label | LIN25.C |
| Description | Linear peptides of length 25 derived from the target sequence of human Clever-1 with an offset of one residue. Cys residues are protected by Acm ("2"). |
| Sequences | (first 10)<br>KKG2ASY2NQTIMEQG22KGFFGPD<br>PD2QSV2S2VHGV2NHGPRGDGS2L<br>GPGQSR2T2KLGFAGDGYQ2SPIDP<br>IFPKE2VYIHDPTGLNVLKKG2ASY<br>PTILPILPKH2SEEQHKIVAGS2VD<br>ENFRGSA2QE2QDPNRFGPD2QSV2<br>QNTQ2SAEAPS2R2LPGYTQQGSE2<br>GRV2VAIDE2ELDMRGG2HTDAL2S<br>APSGTPGDPKRTIGQILASTEAFSR<br>DGMV2LPKDP2TDNLGG2PSNSTL2 |

| Set 5 | |
|---|---|
| Mimic Type | Constrained peptides, mP2 CLIPS |
| Label | LOOP |
| Description | Peptides of length 17. On positions 2-16 are 15-mer sequences derived from the target protein. On positions 1 and 17 are Cys residues joined by mP2 CLIPS. Native Cys residues are protected by Acm ("2"). |
| Sequences | (first 10)<br>CL2SYVGPGQSR2T2KC<br>C2SYVGPGQSR2T2KLC<br>CSYVGPGQSR2T2KLGC<br>CYVGPGQSR2T2KLGFC<br>CVGPGQSR2T2KLGFAC<br>CGPGQSR2T2KLGFAGC<br>CPGQSR2T2KLGFAGDC<br>CGQSR2T2KLGFAGDGC<br>CQSR2T2KLGFAGDGYC<br>CSR2T2KLGFAGDGYQC |

| Set 6 | |
|---|---|
| Mimic Type | Linear disulphide mimics |
| Label | CYS22 |
| Description | Linear disulphide mimics of length 22 designed based on Uniprot information on disulphide bridges for human CLEVER-1. Cys residues within a mimic, that do not participate in disulphide bridge formation, are protected by Acm ("2"). |
| Sequences | (first 10)<br>WGSR2HECPGGAETP2NGHGTC<br>SR2HECPGGAETP2NGHGTCLD<br>2HECPGGAETP2NGHGTCLDGM<br>ECPGGAETP2NGHGTCLDGMDR<br>GAETPCNGHGT2LDGMDRNGTC<br>ETPCNGHGT2LDGMDRNGTCV2<br>PCNGHGT2LDGMDRNGTCV2QE<br>LDGMDRNGT2VC0ENFRGSACQ<br>GMDRNGT2VCQENFRGSACQE2<br>DRNGT2VCQENFRGSACQE2QD |

| Set 7 | |
|---|---|
| Mimic Type | Combinatorial disulphide bridge mimics |
| Label | CYS27 |
| Description | Combinatorial peptides of length 27. On positions 1-11 and 16-27 are 11-mer sequences derived from the target sequence on page 7 joined by "GGSGG" linker. This peptide set was designed based on disulphide bridge information obtained from Uniprot. Cys residues within a mimic, that do not participate in disulphide bridge formation, are protected by Acm ("2"). |
| Sequences | (first 10)<br>PGYWGSR2HECGGSGGAETP2NGHGTC<br>YWGSR2HECPGGGSGGAETP2NGHGTC<br>GSR2HECPGGAGGSGGAETP2NGHGTC<br>R2HECPGGAETGGSGGAETP2NGHGTC<br>HECPGGAETP2GGSGGAETP2NGHGTC |

-continued

Set 7

```
CPGGAETP2NGGGSGGAETP2NGHGTC
PGYWGSR2HECGGSGGTP2NGHGTCLD
YWGSR2HECPGGGSGGTP2NGHGTCLD
GSR2HECPGGAGGSGGTP2NGHGTCLD
R2HECPGGAETGGSGGTP2NGHGTCLD
```

Set 8

| | |
|---|---|
| Mimic Type | Discontinuous matrix, T3 CLIPS |
| Label | MAT |
| Description | Peptides of length 33. On positions 2-16 and 18-32 are 15-mer peptides derived from the target sequence of human Clever-1. On positions 1, 17 and 33 are Cys residues joined by T3 CLIPS. Native Cys residues are protected by Acm ("2"). |
| Sequences | (first 10) |
| | CPNRFGPD2QSV2S2VCV2S2VHGV2NHGPRGC |
| | CHGDGMV2LPKDP2TDCSAG2FAF2SPFS2DRC |
| | C2VD2QALNTST2PPNCPKH2SEEQHKIVAGSC |
| | CPKH2SEEQHKIVAGSCGPD2TQ2PGGFSNP2C |
| | CRYEVQLGGSMVSMSGCVP2TS2AAIKKQT2PC |
| | CHKIVAGS2VD2QALNCIHMLDGILLPPTILPC |
| | CF2T2RPGLVSINSNACVTADGKTS2V2RESEC |
| | C2VYIHDPTGLNVLKKCGSGGV200GT2APGFC |
| | CLRVAVAMMDQG2REICDGRA2YGHLLHEVQKC |
| | CYSYKYKDQPQQTFNICHEVQKATQTGRVFLQC |

Screening Details

Antibody binding depends on a combination of factors, including concentration of the antibody and the amounts and nature of competing proteins in the ELISA buffer. Also, the pre-coat conditions (the specific treatment of the peptide arrays prior to incubation with the experimental sample) affect binding. These details are summed up in Table 2. For the Pepscan Buffer and Preconditioning (SQ), the numbers indicate the relative amount of competing protein (a combination of horse serum and ovalbumin).

TABLE 2

Screening conditions

| Label | Dilution | Sample buffer | Pre-conditioning |
|---|---|---|---|
| 3-266 | 5 µg/ml | 10% SQ | 10% SQ |
| AK FUMM 9-11 | 1 µg/ml | 50% SQ | 50% SQ |
| FAR02 VH3/VK5 | 3 µg/ml | 1% SQ | 1% SQ |
| FU-HI_3-372 | 5 µg/ml | 1% SQ | 1% SQ |

Results
Antibody 3-266

When tested under high stringency conditions antibody 3-266 did not bind any peptides present on the arrays. When tested under low stringency conditions the antibody bound peptides from all sets. Results obtained with simple epitope mimics suggest that sequence $_{1030}$QWLKSAGITLPADRR$_{1044}$ represents the dominant part of the epitope. Data obtained with combinatorial epitope mimics (FIG. 1) suggest that the antibody additionally recognizes sequence $_{857}$LHARCVSQEGVARCIR$_{871}$. Moreover, a weak and consistent signal was recorded for peptides with sequence $_{435}$TMNASLAQQLCRQHI$_{450}$. FIG. 1a illustrates heatmap representation of results obtained for antibody 3-266 on set 8 (discontinuous epitope mimics). Average signal is plotted in black and extremely high signal is plotted in light. Boxed regions are magnified.

Antibody AK FUMM 9-11

Figure 1B:
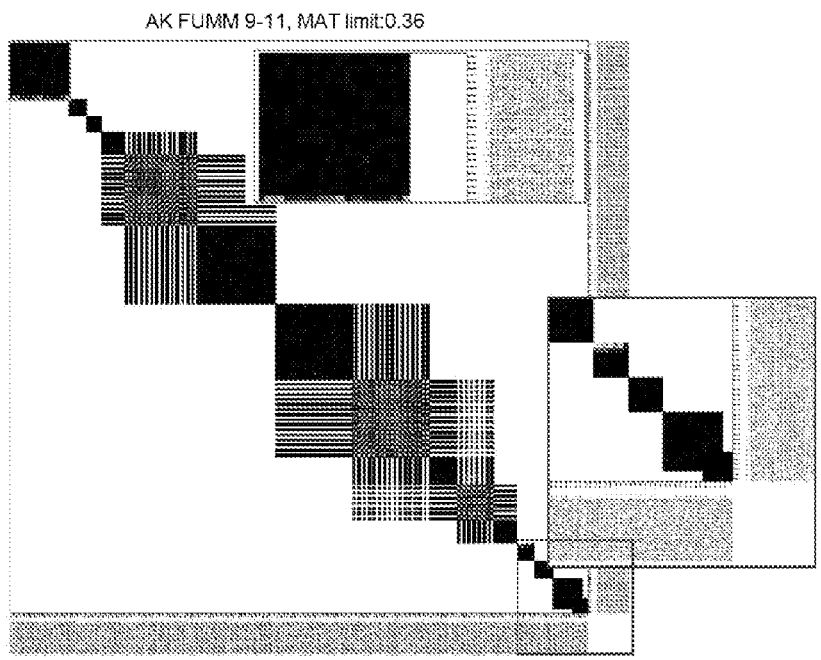

When tested under high stringency conditions antibody AK-FUMM 9-11 bound peptides from all sets. Results obtained with simple epitope mimics suggest that the antibody $_{885}$PSNPCSHPDRGG$_{896}$, which represents the dominant part of epitope. Data obtained with combinatorial epitope mimics suggest that the antibody additionally recognizes combinatorial epitope mimics containing sequence $_{166}$FRGSACQECQDPNRF$_{180}$ (FIG. 1b). FIG. 1b illustrates heatmap representation of results obtained for antibody AK FUMM 9-11 on set 8 (discontinuous epitope mimics). Average signal is plotted in black and extremely high signal is plotted in light. Boxed regions are magnified.

Antibody FAR02 VH3/VK5 and FU-HI:3-372

Figure 2:
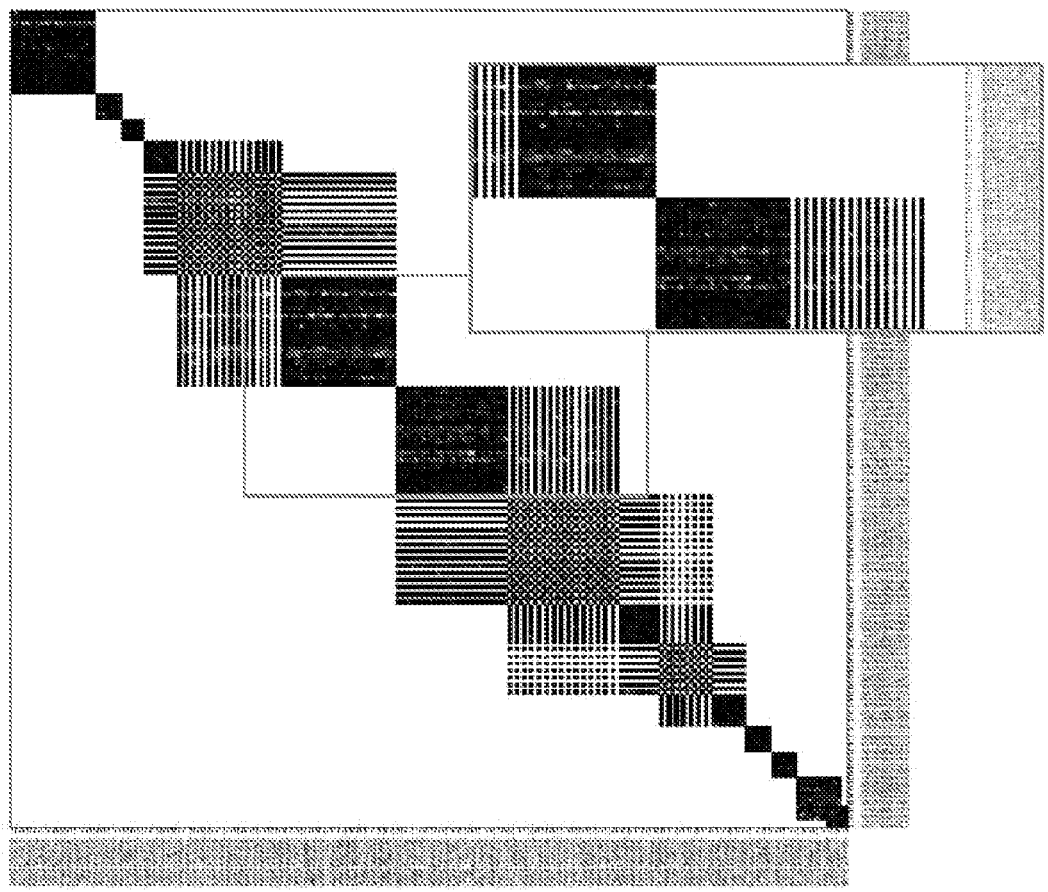
FIG. 2 illustrates heatmap representation of results obtained for antibody FU—HI-3-372.

When tested under high stringency conditions antibodies FAR02 VH3/vk5 and FU—HI-3-372 did not bind any peptides present on the arrays. When tested under low stringency conditions these antibodies specifically bound peptides only from set 8 (FIG. 2). Analysis of results obtained with discontinuous mimics suggests that the antibody recognizes a discontinuous epitope composed of sequences $_{390}$ATQTGRVFLQ$_{399}$ (SEQ ID NO: 3), $_{420}$PFTVLVPSVSSFSSR$_{434}$ (SEQ ID NO: 1), $_{473}$QEITVTFNQFTK$_{484}$ (SEQ ID NO: 2), $_{576}$DSLRDGRLIYLF$_{587}$ (SEQ ID NO: 4), $_{615}$SKGRILTMANQVL$_{627}$ (SEQ ID NO: 5), where sequences $_{473}$QEITVTFNQFTK$_{484}$ (SEQ ID NO: 2) and $_{420}$PFTVLVPSVSSFSSR$_{434}$ (SEQ ID NO: 1) appear to represent core epitopes. Additional weaker signal was recorded for discontinuous mimics containing sequence $_{313}$LCVYQKPGQAFCTCR$_{327}$ (SEQ ID NO: 6). Results obtained with simple epitope mimics do not allow epitope calling. FIG. 2 illustrates heatmap representation of results obtained for antibody FU—HI-3-372 on set 8 (discontinuous epitope mimics). Average signal is plotted in black and extremely high signal is plotted in light. Boxed regions are magnified.

CONCLUSIONS

The antibodies were tested against Pepscan peptide arrays. It was possible to identify tentative discontinuous epitopes for all monoclonal antibodies. Peptide sequences comprising epitopes are listed in Table 3. Antibodies 3-266 and AK FUMM 9-11 bind distinct discontinuous epitopes. Antibodies FAR02 VH3/VK5 and FU—HI-3-372 essentially displayed highly similar binding patterns when tested on the arrays and, therefore, were shown to recognize the same discontinuous epitope in the FAS1/FAS2 domains.

TABLE 3

Epitopes found

| Antibody | Epitope sequences | Domain |
|---|---|---|
| 3-266 | $_{1030}$QWLKSAGITLPADRR$_{1044}$ | FAS 3 |
| | $_{857}$LHARCVSQEGVARCR$_{871}$ | EGF-like 6 |
| | $_{435}$TMNASLAQQLCRQHI$_{450}$ | FAS 1 |
| AK FUMM 9-11 | $_{885}$PSNPCSHPDRGG$_{896}$ | EGF-like 6 |
| | $_{166}$FRGSACQECQDPNRF$_{180}$ | EGF-like 1 |

TABLE 3-continued

Epitopes found

| Antibody | Epitope sequences | Domain |
|---|---|---|
| FAR02 VH3/VK5 + | $_{420}$PFTVLVPSVSSFSSR$_{434}$ | FAS 1 |
| FU-HI-3-372 | $_{473}$QEITVTFNQFTK$_{484}$ | FAS 1 |
| | $_{390}$ATQTGRVFLQ$_{399}$ | FAS 1 |
| | $_{576}$DSLRDGRLIYLF$_{587}$ | FAS 2 |
| | $_{615}$SKGRILTMANQVL$_{627}$ | FAS 2 |

Figure 3:
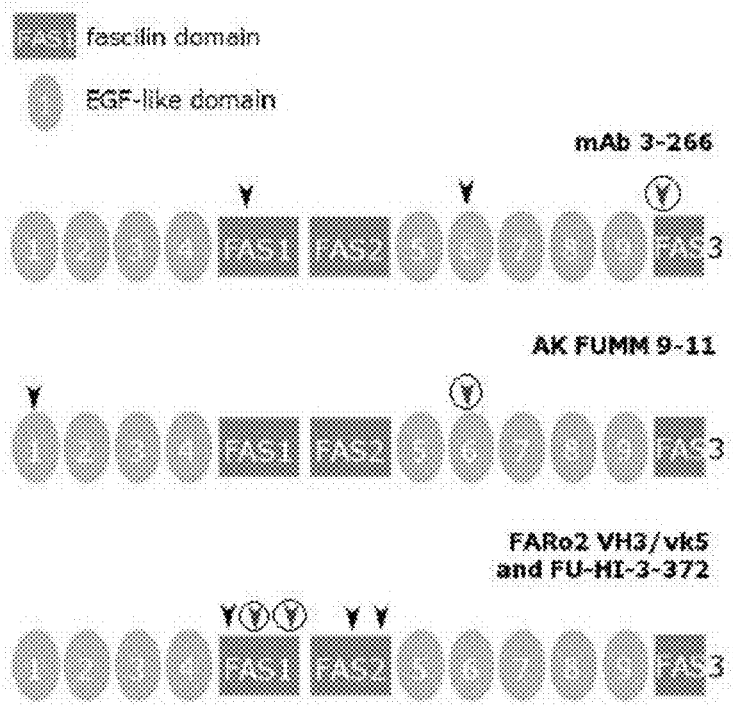
FIG. 3 illustrates schematically the domain organization of CLEVER-1 positions of identified binding motifs.

To compare visually tentative epitopes identified for the above mentioned antibodies a schematic drawing in FIG. 3 was used. This schematic was adapted from FIG. 1 from Kzhyshkowska, *TheScientificWorldJOURNAL* (2010) 10, 2039-2053 representing Stabilin-1 (CLEVER-1) domain organization. FIG. 3 illustrates schematically the domain organization of CLEVER-1 (aa_25-1027 as per target sequence). Arrowheads indicate relative positions of identified binding motifs. Circulated arrowheads indicate positions of dominant epitope cores.

Figure 4:
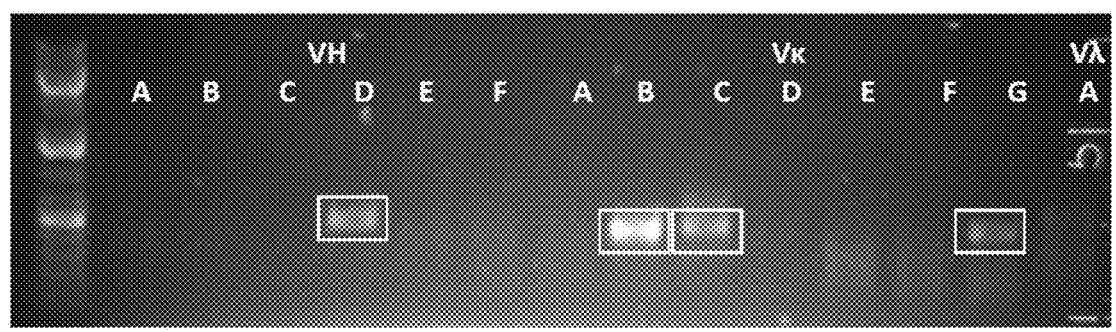
FIG. 4 illustrates 1% agarose gel separation of hybridoma 3-372 RT-PCR products.

Example 2 mRNA Extraction, RT-PCR and Cloning mRNA was successfully extracted from the hybridoma cells (PolyA Tract system, Promega Cat. No. Z5400). RT-PCR was performed using degenerate primer pools for murine signal sequences with a single constant region primer. Heavy chain variable region mRNA was amplified using a set of six degenerate primer pools (HA to HF) and light chain variable region mRNA was amplified using a set of eight degenerate primer pools (κA to κG and λA). Amplification products were obtained with the heavy chain primer pool HD and light chain primer pools κB, κC and κG confirming the light chain is from the κ cluster (FIG. 4). Each product was cloned and several clones from each sequenced.

Using this methodology, a single VH sequence [SEQ ID NO: 32 (base sequence) and NO: 33 (amino acid sequence)] was identified in pool HD and a single functional Vκ sequence [SEQ ID NO: 34 (base sequence) and NO: 35 (amino acid sequence)] was identified in primer pool κG. The CDRs of the heavy chain stretch from base 91 to 111 (SEQ ID NO: 7), 154 to 210 (SEQ ID NO: 8) and 298 to 333 (SEQ ID NO: 9); and the CDRs of the light chain stretch from base 70 to 105 (SEQ ID NO: 10), 151 to 171 (SEQ ID NO: 11) and 268 to 294 (SEQ ID NO: 12). CDR definitions and protein sequence numbering are according to Kabat. An aberrant κ light chain transcript normally associated with the hybridoma fusion partner SP2/0 (GenBank M35669) was also identified in primer pools κB and κC.

FIG. 4 illustrates 1% agarose gel separation of hybridoma 3-372 RT-PCR products. Gel was stained with SYBR® Green dye (Invitrogen Cat. No. S-7567) and photographed over ultraviolet light. Size marker is GeneRuler™ 1 Kb Plus (Fermentas Cat. No. SM1331). Boxes indicate bands that were isolated for cloning and sequencing.

Example 3

Sequence Analysis

The analysis of the sequences obtained from hybridoma expressing 3-372 is summarised in Table 4.

TABLE 4

| 3-372 Antibody Sequence Analysis[a] | | |
|---|---|---|
| | H-Chain | L-Chain |
| CDR 1 Length | 7aa | 12aa |
| CDR 2 Length | 16aa | 7aa |
| CDR 3 Length | 12aa | 9aa |
| Closest Human Germline[b] | IGHV2-5*10 (73%) | IGKV3D-20*01 (65%) |
| Closest Human FW1[b] | IGHV2-70*06 (73%) | IGKV1D-17*01 (68%) |
| Closest Human FW2[b] | IGHV2-5*09 (86%) | IGKV1D-39*01 (73%) |
| Closest Human FW3[b] | IGHV2-70*13 (72%) | IGKV1D-43*01 (78%) |
| Closest Human J[b] | IGHJ1 (91%) | IGKJ4 (80%) |

[a]CDR definitions and sequence numbering according to Kabat
[b]Germline ID(s) indicated followed by % homology Structure and homology analysis of the murine 3-372 variable domain sequence identified four framework residues in the heavy chain variable region and five framework residues in the light chain variable region which were considered to be critical or possibly important to antigen binding ("constraining residues"). Additional sequence database analysis revealed that human framework segments can be found to include all desirable constraining residues and all CDR residues, thus permitting the construction of Composite Human Antibodies™.

It was also noted that the 3-372 V-regions contain some unusual features. The VH chain contains a N-glycosylation site at the beginning of CDR1 since residue 30 is N and 32 is S (N-glycosylation signal is NXS or NXT, where X can be any amino acid). Due to the likely exposure of this motif on the surface of the antibody, it is probable that this site will be glycosylated. Therefore it would be advantageous (if not involved in antigen binding) to avoid this site in the Composite Human Antibodies in order to avoid any manufacturing issues in the future. The $V_\kappa$ chain also contains a glycosylation site but only in the context of a human κ constant region since the final amino acid of the $V_\kappa$ domain is asparagine. The mouse κ constant domain begins RA, whereas the human κ constant domain begins RT, thus forming a glycosylation signal. Therefore sequences for Composite Human Antibodies will be selected to avoid this asparagine.

The κ domain also contains an unpaired cysteine at position 47. Molecular modelling suggest that this residue will be buried within the structure and therefore not available for disulphide bonding; however it could be a key residue for maintaining the conformation of $V_\kappa$ CDR2, and therefore sequences for Composite Human Antibodies will be selected with and without this residue (the latter including the consensus human L at this position) in order to investigate its effects on antigen binding.

Example 4

Expression of Chimeric Antibody

The 3-372 variable regions were transferred to Antitope's expression vector system for IgG4(S241P) heavy chain and kappa light chain. NS0 cells were transfected via electroporation and selected using methotrexate (MTX). A number of MTX resistant colonies were identified using an Fc capture/kappa chain detection ELISA, and cell lines positive for IgG expression were expanded continuously from 96-well plates through to T175 flasks in media containing gradually increasing concentrations of MTX and subsequently frozen under liquid nitrogen. At each stage, IgG expression was quantified.

Figure 5:
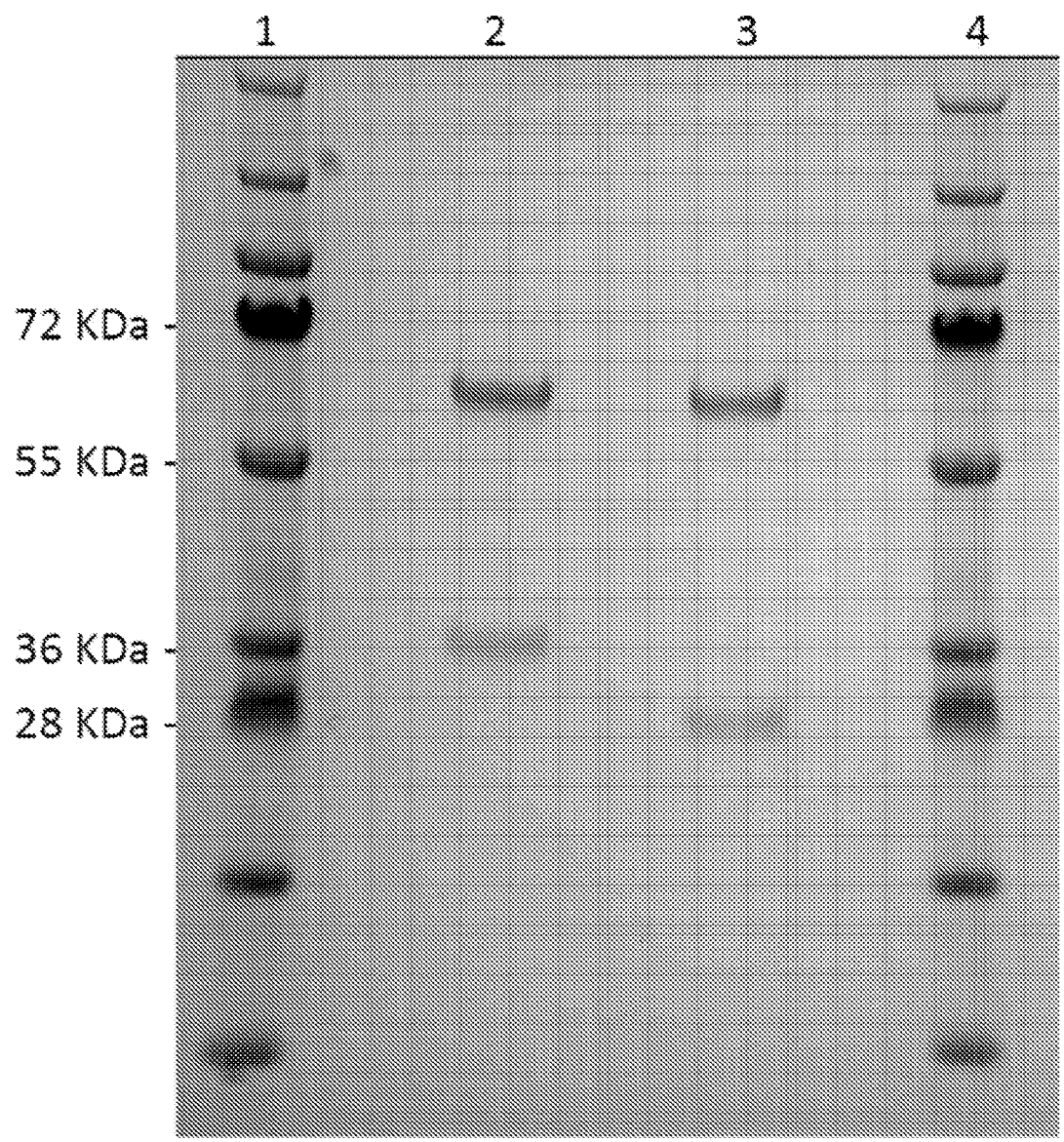
FIG. 5 illustrated Coomassie Blue-stained SDS-PAGE gel of protein A-purified chimeric 3-372 IgG4.

Chimeric 3-372 IgG4 was purified from cell culture supernatants on a Protein-A Sepharose column and quantified by OD280 nm using an extinction coefficient (Ec (0.1%)) value of 1.55 based on the predicted amino acid sequence for chimeric IgG4. Approximately 90 µg of antibody was purified and a sample was analysed by reducing SDS-PAGE (FIG. 5). Bands corresponding to the predicted sizes of the heavy and light chains were observed with no evidence of any contamination; however it was notable that the chimeric light chain appears to be glycosylated as evidenced by the greater apparent molecular weight than the mouse light chain. The heavy chain also appeared to be running slower than is usual, suggesting that it is also N-glycosylated; however digestion with glycosidases would be required to demonstrate that this is indeed the case.

FIG. 5 illustrates Coomassie Blue-stained SDS-PAGE gel of protein A-purified chimeric 3-372 IgG4. 1 µg of sample was loaded on a NuPage 4-12% Bis-Tris gel (Invitrogen Cat. No. NP0322BOX) and run at 200 V for 30 min. Lanes 1&4: Prestained protein standard (Fermentas PageRuler Cat. No. SM1811). Lane 2: 1.0 µg chimeric 3-372 IgG4 antibody. Lane 3 1.0 µg murine 3-372 antibody.

Example 5

Binding of Chimeric Antibody to CLEVER-1

The binding of NS0 derived chimeric 3-372 to CLEVER-1 was assessed by competition ELISA. Briefly, a Nunc Immulon 96 well maxisorp plate (Fisher Cat. No. DIS-971-030J) was coated with CLEVER-1 at 1 µg/ml in PBS (100 µl/well) overnight at 4° C., with an additional 1 hour at 37° C. the following morning. Wells were washed with PBS/0.1% Tween 20 and then blocked for 45 min at room temperature, in 1% Marvel/1% BSA/PBS.

Dilution series of both the chimeric 3-372 and the reference mouse 3-372 (5-0.078 µg/ml) were premixed with a constant concentration (0.6 µg/ml) of biotinylated mouse 3-372 antibody in 2% BSA/PBS. The blocked ELISA plate was washed as before and 100 µl of the premixed antibodies added to each well. The plate was incubated for 1 hour at room temperature. Binding of the biotinylated mouse 3-372 to CLEVER-1 was detected using Streptavidin-HRP (Sigma Cat. No. S5512) and TMB single solution substrate (Invitrogen Cat. No. 00-2023). The reaction was stopped with 3M HCl, absorbance read at 450 nm on a Dynex Technologies MRX TC II plate reader and the binding curve of the chimeric 3-372 compared to that of the reference mouse 3-372 antibody (FIG. 6).

Figure 6:
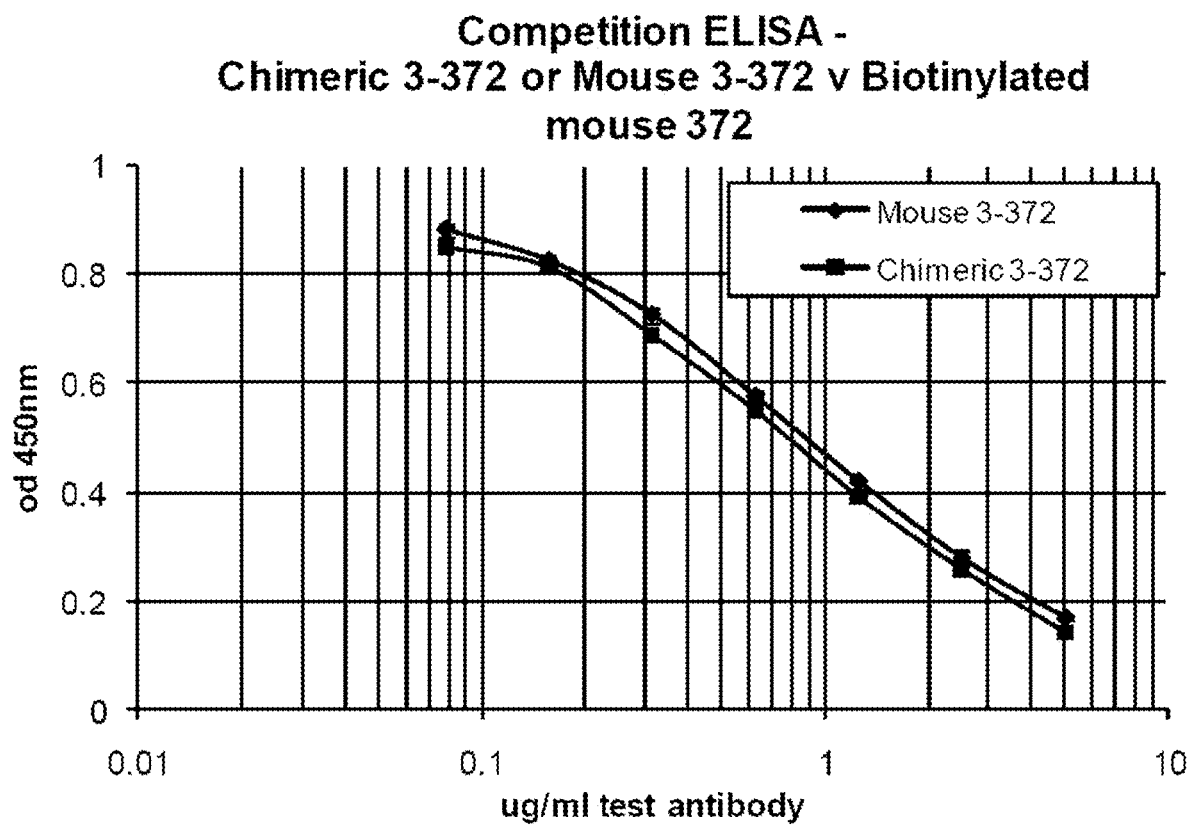
FIG. 6 illustrates CLEVER-1 competition ELISA.

FIG. 6 shows the binding profile of the mouse and chimeric antibodies for CLEVER-1 in competition with the biotinylated mouse antibody. The curves are almost identical giving IC50 values of 0.89 µg/ml for the chimeric antibody compared to 0.77 µg/ml for the mouse antibody. This confirms that the correct variable region sequences have been identified and expressed in the chimeric antibody.

Example 7

Design of Composite Human Antibody™ Variable Region Sequences and Variants

Structural models of the murine anti-CLEVER-1 antibody V regions were produced using Swiss PDB and analysed in order to identify important "constraining" amino acids in the V regions that were likely to be essential for the binding properties of the antibody. Residues contained within the CDRs (using both Kabat and Chothia definitions) together with a number of framework residues were considered to be important. Both the VH and V$_\kappa$ sequences of anti-Clever 1 contain typical framework residues and the CDR 1, 2 and 3 motifs are comparable to many murine antibodies. However, we identified a potential site for N-linked glycosylation in the VH sequence (30N), and an unpaired cysteine in the Vκ sequence (47C).

From the above analysis, it was considered that composite human sequences of anti-CLEVER-1 could be created with a wide latitude of alternatives outside of the CDRs but with only a narrow menu of possible alternative residues within the CDR sequences. Preliminary analysis indicated that corresponding sequence segments from several human antibodies could be combined to create CDRs similar or identical to those in the murine sequences. For regions outside of and flanking the CDRs, a wide selection of human sequence segments were identified as possible components of the novel Composite Human Antibody™ V regions.

Based upon the above analysis, a large preliminary set of sequence segments that could be used to create anti-CLEVER-1 Composite Human Antibody™ variants were selected and analysed using iTope™ technology for in silico analysis of peptide binding to human MHC class II alleles (Perry et al 2008), and using the TCED™ (T Cell Epitope Database) of known antibody sequence-related T cell epitopes (Bryson et al 2010). Sequence segments that were identified as significant non-human germline binders to human MHC class II or that scored significant hits against the TCED™ were discarded. This resulted in a reduced set of segments, and combinations of these were again analysed, as above, to ensure that the junctions between segments did not contain potential T cell epitopes. Selected segments were then combined to produce heavy and light chain V region sequences for synthesis. For anti-CLEVER-1, four VH chains, VH1, VH2; VH3 and VH4 [SEQ ID NO: 13, 15, 17 and 19 (base sequence) and NO: 14, 16, 18 and 20 (amino acid sequence), respectively] and five Vκ chains, Vκ1, Vκ2, Vκ3, Vκ4 and Vκ5 [SEQ ID NO: 21, 23, 25, 27 and 29 (base sequence) and NO: 22, 24, 26, 28 and 30 (amino acid sequence), respectively] were designed. The heavy chain CDRs VH1, VH2, VH3 and VH4 stretch from base 91 to 111, 154 to 201 and 298 to 333; and the light chain CDRs VK1, VK2, VK3, VK4 and VK5 stretch from base 70 to 105, 151 to 171 and 268 to 294. CDR definitions and protein sequence numbering are according to Kabat. Of note, three of the VH chains have the potential N-linked glycosylation site removed (VH2, VH3, and VH4), and two of the Vκ chains have the unpaired cysteine removed (VK4 and VK5).

Example 8

Construction of Composite Human Antibody™ Variants

Figure 7:
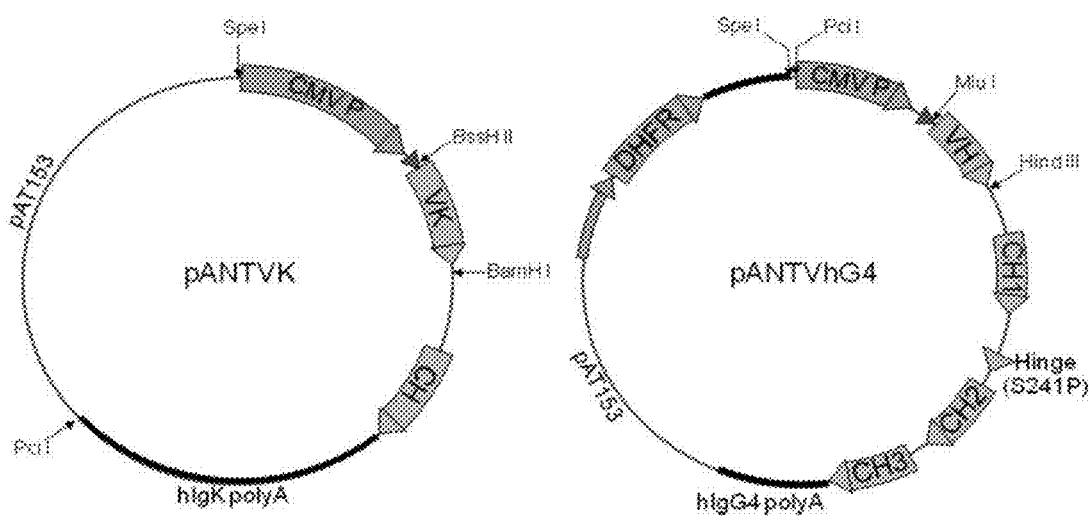
FIG. 7 illustrates Antitope pANT vector diagram.

All variant Composite Human Antibody™ VH and Vκ region genes for anti-Clever 1 were synthesized using a series of overlapping oligonucleotides that were annealed, ligated and PCR amplified to give full length synthetic V regions. The assembled variants were then cloned directly into Antitope's pANT expression vector system for IgG4 (S241P) VH chains and Vκ chains (FIG. 7). The VH region was cloned using MluI and HindIII sites, and the Vκ region was cloned using BssHII and BamHI restriction sites. All constructs were confirmed by sequencing.

FIG. 7 shows the Antitope pANT vector diagram. Both Vh and VK vectors contain genomic DNA fragments incorporating introns and poly A sequences. Expression of both chains is driven by a CMV promoter and selection (on the heavy chain vector) is via a DHFR mini gene.

Example 9

Construction, Expression and Purification of Antibodies

All combinations of composite IgG4(S241P) VH and Vκ chains (i.e. a total of 20 pairings) were stably transfected into NS0 cells via electroporation. The stable transfections were selected using 200 nM methotrexate (MTX) (Sigma cat. no. M8407), methotrexate-resistant colonies for each construct were tested for IgG expression levels using an IgG4 ELISA, and the best expressing lines were selected, expanded and frozen under liquid nitrogen. Successful transfection and stable clone selection were achieved for all variants except VH3/Vκ3 and VH4/Vκ3.

The composite variants of anti-CLEVER-1 were purified from cell culture supernatants on a Protein A sepharose column (GE Healthcare cat. no. 110034-93), buffer exchanged into a PBS and quantified by OD280 nm using an extinction coefficient (Ec (0.1%)=1.55) based on the predicted amino acid sequence. The lead Composite Human Antibody™ variants were analysed by reducing SDS-PAGE. Bands corresponding to the predicted sizes of the VH and Vκ chains were observed with no evidence of any contamination (FIG. 8).

Figure 8:
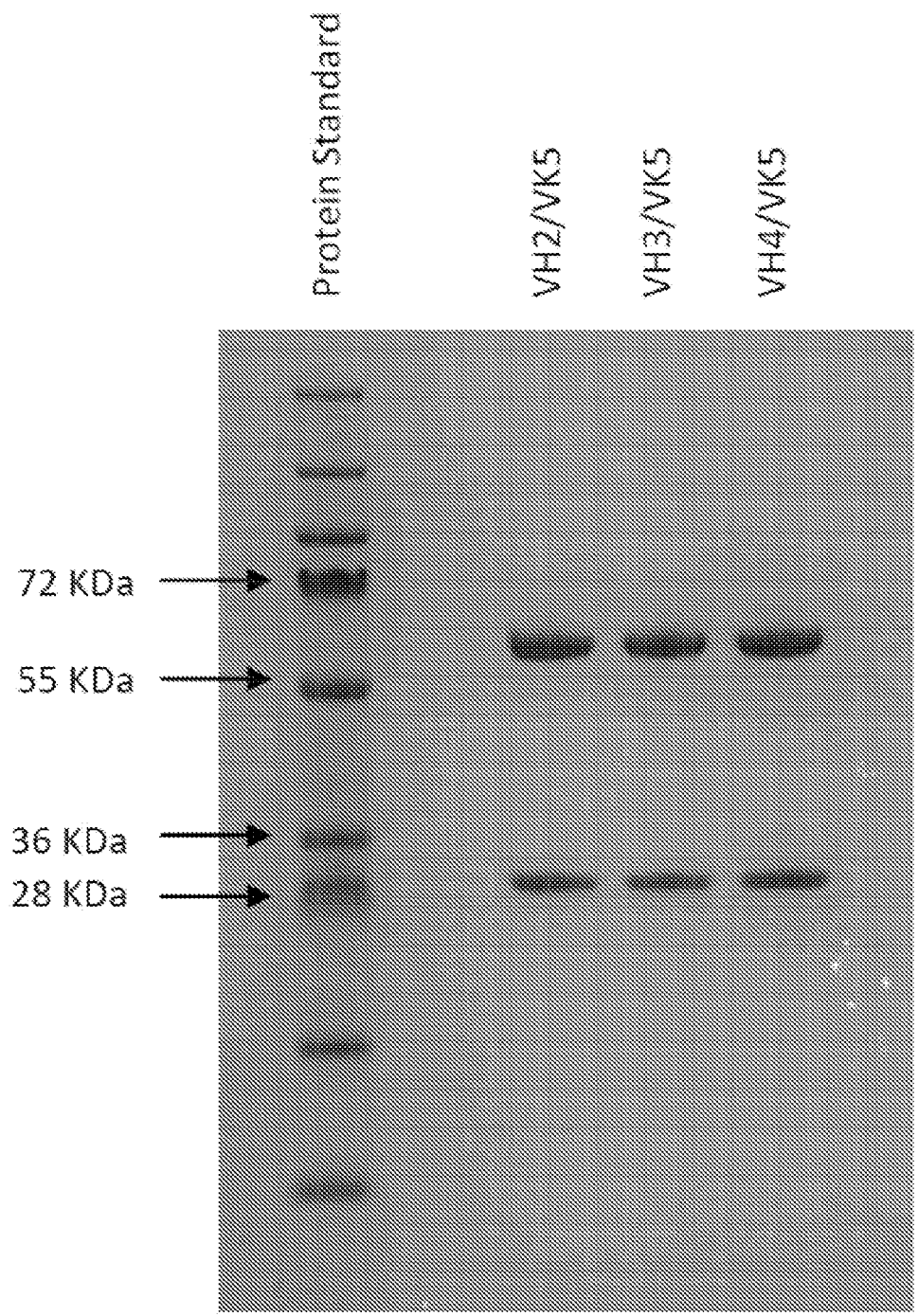
FIG. 8 illustrates Coomassie Blue-stained SDS-PAGE gel of selected protein A-purified antibodies.

FIG. 8 illustrates Coomassie Blue-stained SDS-PAGE gel of selected protein A-purified antibodies. 2 μg of each sample was loaded on a NuPage 4-12% Bis-Tris gel (Invitrogen cat. no. NP0322BOX) and run at 200 V for 35 min. Size marker is prestained protein standard Fermentas PageRuler (cat. no. SM1811).

Example 10

Binding of Composite Human Antibodies™ to CLEVER-1

The binding of NS0 derived Composite 3-372 antibodies to CLEVER-1 was assessed by competition ELISA. Dilution series of the chimeric and the composite 3-372 antibodies (5-0.078 μg/ml) were premixed with a constant concentration (0.6 μg/ml) of biotinylated Mouse 3-372 antibody. These were incubated for 1 hour at room temperature on a 96 well Immulon maxisorp plate (Fisher Cat. No. DIS-971-030J) precoated with 14/ml CLEVER-1. Binding of the biotinylated Mouse 3-372 to CLEVER-1 was detected using Streptavidin-HRP (Sigma Cat. No. S5512) and TMB single solution substrate (Invitrogen Cat. No. 00-2023). The reaction was stopped with 3M HCl, absorbance read at 450 nm on a Dynex Technologies MRX TC II plate reader and the binding curves plotted. IC50 values for each antibody were calculated and these were normalized to the IC50 of the chimera which was included on each respective ELISA plate.

Figure 9:
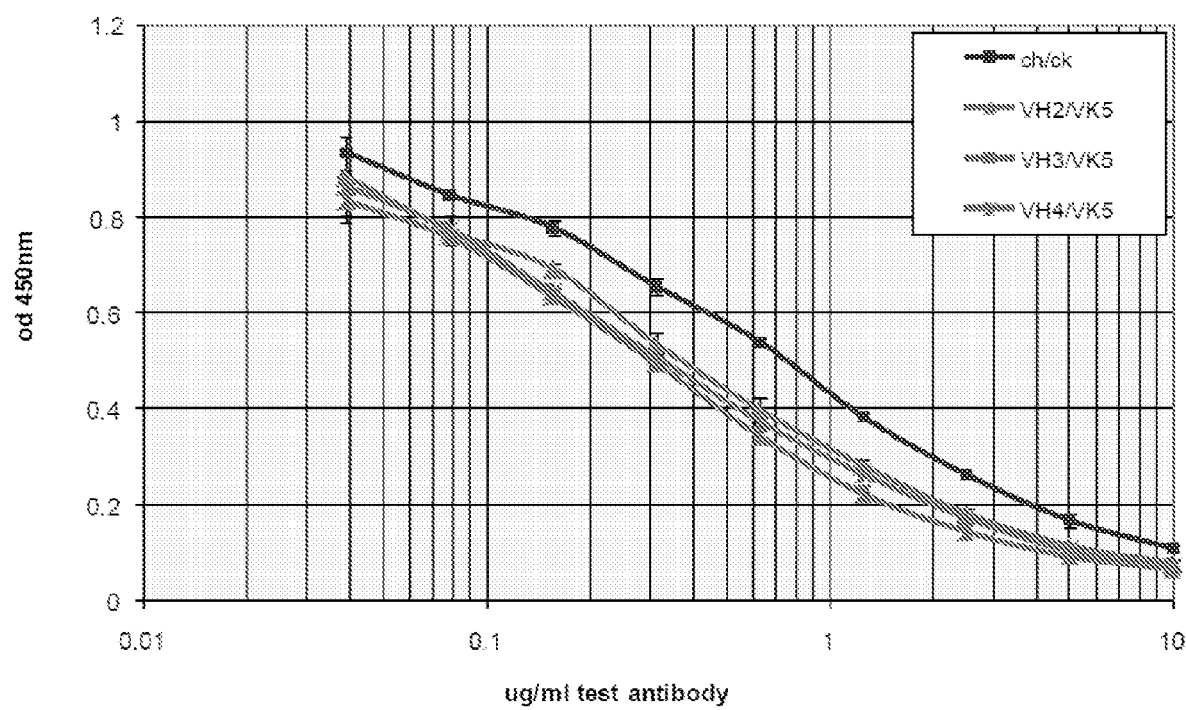
FIG. 9 illustrates CLEVER-1 competition ELISA.

The IC50s obtained show a number of the Composite Human Anti-CLEVER-1 Antibodies™ has better binding to CLEVER-1 than the chimeric 3-372. Competition data for the lead variants is shown in FIG. 9.

TABLE 5

Binding characterisation of Composite Human anti-CLEVER-1 Antibodies™

| V Region IDs | Relative $IC_{50}$ |
|---|---|
| CH/CK | 1.0 |
| VH1/VK1 | 0.84 |
| VH1/VK2 | 1.37 |
| VH1/VK3 | 1.63 |
| VH1/VK4 | 1.17 |
| VH1/VK5 | 1.13 |
| VH2/VK1 | 0.82 |
| VH2/VK2 | 0.95 |
| VH2/VK3 | 0.7 |
| VH2/VK4 | 0.79 |
| VH2/VK5 | 0.52 |
| VH3/VK1 | 0.76 |
| VH3/VK2 | 0.51 |
| VH3/VK3 | — |
| VH3/VK4 | 0.47 |
| VH3/VK5 | 0.42 |
| VH4/VK1 | 1.86 |
| VH4/VK2 | 0.9 |
| VH4/VK3 | — |
| VH4/VK4 | 1.2 |
| VH4/VK5 | 0.46 |

The relative $IC_{50}$ was calculated by dividing the value for the test antibody by that of the chimera assayed on the same plate.

Example 11: Antibody Binding In Vitro

Human peripheral blood monocytes from healthy donors were collected and they were enriched from about 9 ml of peripheral blood by Ficoll-gradient centrifugation. After that they are plated in low attachment 96-well plates in a density of 1.2×106 cell/well in IMDM medium supplemented with 1% human AB serum. The cells were treated with 1 μg/ml or 10 μg/ml of anti-CLEVER-1 antibody 3-372 (DSM ACC2520 deposited at DSMZ-Deutsche Sammlung von Mikroorganismen und Zellkulturen GmbH on Aug. 21, 2001) or VH3/VK5 (a humanized anti-CLEVER-1 antibody according to the present invention recognizing said specific CLEVER-1 epitope) for 48 hours. HLA-DR expression was determined from CD14 positive cells after 48 hours by using LSR Fortessa flow cytometry. Dead cells were eliminated from the analysis based on the positive signal for 7-AAD cell viability dye.

Human IgGs was used as reference.

Figure 10:
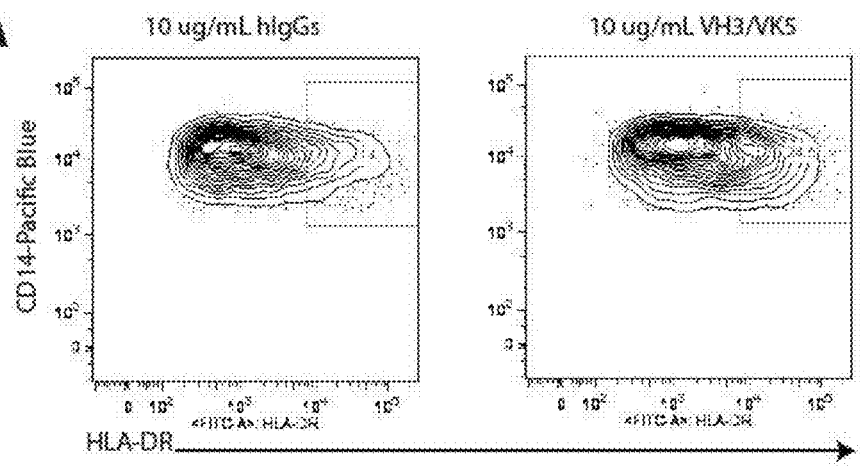
FIG. 10A shows results of the determination of HLA-DR expression from CD14 positive cells and FIG. 10B shows results of soluble TNF-alpha measured from the culture medium using a TNF-alpha ELISA kit (Invitrogen).
Figure 10:
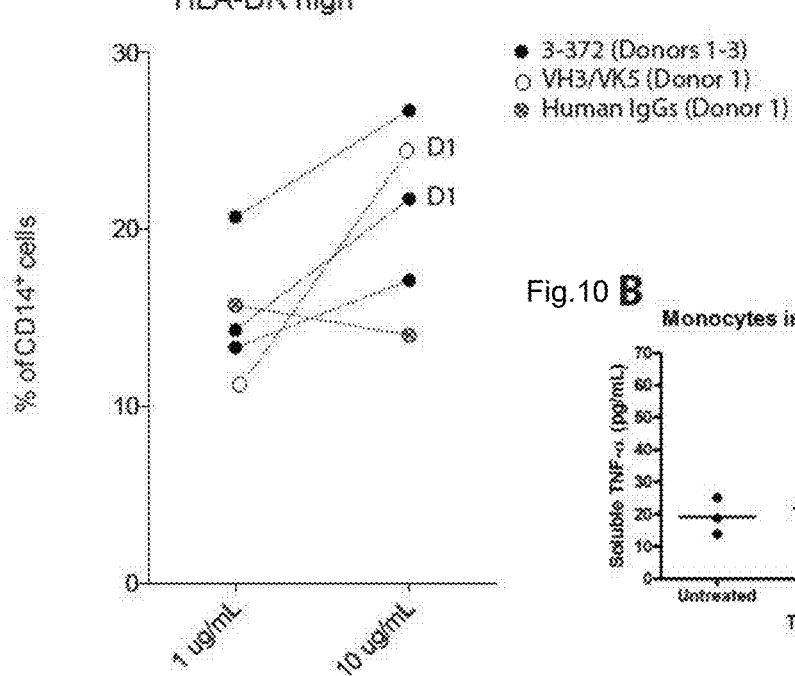
Figure 10:
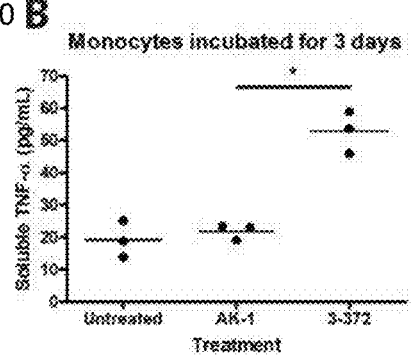

FIG. 10A shows results of the determination HLA-DR expression from CD14 positive cells. HLA-DR expression on CD14 positive cells increased with treatment of humanized anti-CLEVER-1 antibody VH3/VK5 compared to reference of human IgGs.

No difference in cell viability between treatments was observed. Thus, it can be concluded that the CLEVER-1 targeting antibodies do not affect monocyte survival.

Example 12: Measurement of TNF-α

Human peripheral blood monocytes from healthy donors were collected and enriched as described in Example 11. Monocytes from 3 ml of erythrocyte lysis buffer treated blood were let to adhere overnight on 6-well plates, washed once with PBS and cultured for 3 days with 10 μg/ml of anti-CLEVER-1 antibody 3-372 or AK-1.

Soluble TNF-alpha was measured from culture medium using a commercial TNF-alpha ELISA kit (Invitrogen). The results of the measurement are showed in FIG. 10B. The increased TNF-alpha secretion has noticed by samples treated with anti-CLEVER-1 antibody compared to untreated samples or the control treated samples with AK-1.

Example 13: Mouse Syngeneic Cancer Models

Established E0771 mouse mammary carcinomas were treated with 5 mg/kg of anti-CLEVER-1 (mStab1) or isotype control every 3-4 days until the tumours reached a size of 1 mm$^3$. The effect of anti-CLEVER-1 treatment on the recruitment and phenotype of TAMs, different monocyte subsets and tumour-infiltrating leukocytes was assessed using flow cytometry.

Figure 11A:
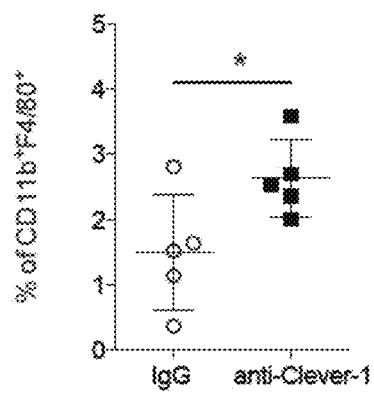
FIG. 11A shows TAM re-polarization in syngeneic E0771 mammary carcinomas after administration of an antibody binding to CLEVER-1 and FIG. 11B shows increased secretion of TNF-alpha on TAMs from E0771 syngeneic mammary carcinoma after administration of an antibody binding to CLEVER-1.

FIG. 11A shows TAM re-polarization in syngeneic E0771 mammary carcinomas after administration of an antibody binding to CLEVER-1. TAM re-polarization is measured by increased macrophage populations expressing MHCII (in human HLA-DR) by flow cytometry. Each dot represents the percentage of MHCII$^{high}$ CD11$^+$F4/80$^+$ TAMs in one mouse. Tumours treated with anti-CLEVER-1 showed a similar level of TAMs (CD11b+F4/80+) compared to the control treated tumours. However, the TAM population in anti-CLEVER-1 tumours consisted of more pro-inflammatory macrophages (Ly6CloMHCIIhi) with lower expression of the type II marker, CD206.

Figure 11B:
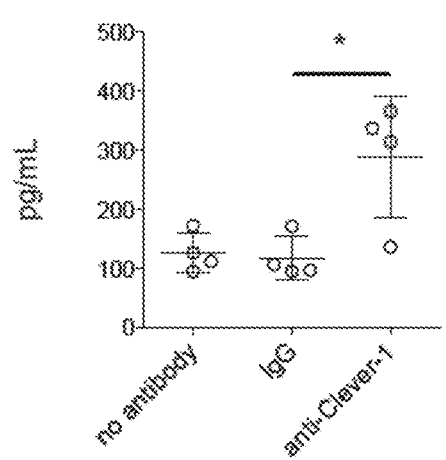

The anti-CLEVER-1 treated TAMs secreted significantly more TNF-alpha compared to IgG treated TAMs, as shown in FIG. 11B. Each dot represents TAMs isolated from one mouse. Consistent with this, also a decrease in FoxP3+ tumour-infiltrating leukocytes was observed.

The results indicate that CLEVER-1 is a potential target for macrophage-directed immunotherapy.

Example 14

Figure 12:
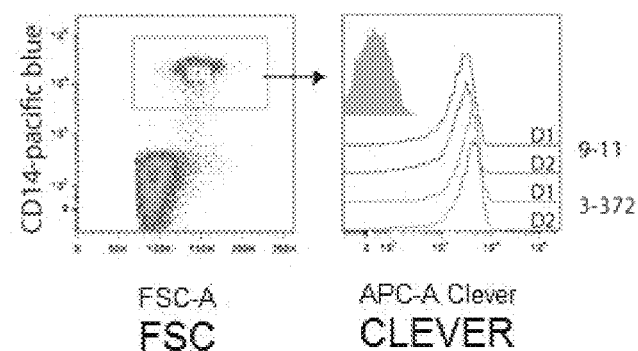
FIGS. 12A and 12B illustrate that CLEVER-1 ligation with 9-11 and 3-372 antibodies promotes opposing effects on mTOR and c-Jun signalling in human peripheral blood monocytes.
Figure 12:
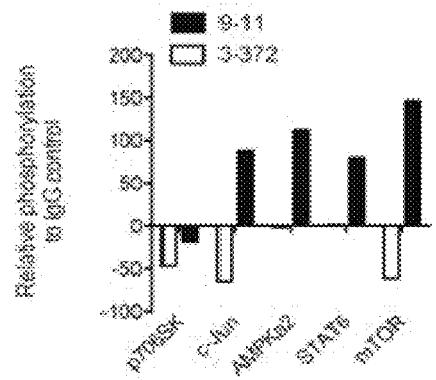

As in example 1 has denoted, the antibodies 9-11 and 3-372 binds to distinct epitopes in human CLEVER-1 and now it has studied the effects of this difference on signaling in human peripheral blood monocytes. FIG. 12 illustrates that CLEVER-1 ligation with 9-11 and 3-372 antibodies promotes opposing effects on mTOR (mechanistic target of rapamycin) and c-Jun signaling in human peripheral blood monocytes.

FIG. 12A shows flow cytometry analysis of 9-11 and 3-372 binding on CD14 positive human monocytes (n=2 donors, D1 and D2).

FIG. 12B shows results, when Human Phospho-Kinase Array (R&D) was used to measure activation of phospho proteins on CD14 positive cells (enriched by negative selection) after a 10 minute treatment with 20 µg/mL of 9-11 and 3-372. The phospho signals were normalized to relevant isotype control treated cells, ratIgG2a for 9-11 and mouse IgG1 for 3-372. As shown in FIG. 12B, antibodies 9-11 and 3-372 promote opposing effects on mTOR and c-Jun signaling in human peripheral blood monocytes. It is known that the mTOR pathway regulates macrophage polarization and immunosuppressive macrophage phenotype depends on c-Jun phosphorylation, wherein the results indicate that 3-372 antibody activates macrophages to switch their phenotype from M2 macrophages into M1 macrophages.

Other Preferred Embodiments

It will be appreciated that the agent capable of binding to human CLEVER-1, suc as an antibody, the single chain Fv or Fab fragment(s), peptide(s), macromolecule(s), and humanized antibody or humanized single chain Fv or Fab fragment(s) and pharmaceutical compositions of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

The invention claimed is:

1. A method for treating a patient having a cancer that has CLEVER-1 positive cells in the tumor microenvironment, the method comprising administering a humanized antibody or single chain Fv or Fab fragment capable of binding to human CLEVER-1 to the patient, wherein said humanized antibody or single chain Fv or Fab fragment comprises the following sequences of complementarity determining regions (CDRs)

i) of the heavy chain
CDR 1:
                                        (SEQ ID NO: 7)
TSGMGIG, CDR 2:
                                        (SEQ ID NO: 8)
HIWWDDDKRYNPALKS,
and CDR 3:
                                        (SEQ ID NO: 9)
HYGYDPYYAMDY;
and ii) of the light chain
CDR 1:
                                        (SEQ ID NO: 10)
TASSSVSSSYLH, CDR 2:
                                        (SEQ ID NO: 11)
RTSNLAS,
and

CDR 3:
                                        (SEQ ID NO: 12)
HQYHRSPPT.

2. The method according to claim 1, wherein the humanized antibody or single chain FV or Fab fragment comprises constant regions of human IgG4 heavy chain and kappa light chain.

3. The method according to claim 1, wherein the humanized antibody or single chain Fv or Fab fragment comprises a human IgG heavy chain variable region sequence comprising an amino acid sequence selected from the group consisting of SEQ ID NO: 14, SEQ ID NO: 16, SEQ ID NO 18 and SEQ ID NO: 20, and a human IgG light chain variable region comprising an amino acid sequence selected from the group consisting of SEQ ID NO: 22, SEQ ID NO: 24, SEQ ID NO: 26, SEQ ID NO: 28 and SEQ ID NO: 30.

4. The method according to claim 3, wherein the humanized antibody or the single chain Fv or Fab fragment is capable of binding to human CLEVER-1 with a relative IC50<1.0 in comparison to the IC50 of monoclonal antibody 3-372 (DSM ACC2520 deposited at DSMZ-Deutsche Sammlung von Mikroorganismen und Zellkulturen GmbH on Aug. 21, 2001).

5. The method according to claim 3, wherein the humanized antibody or the single chain Fv or Fab fragment is capable of binding to human CLEVER-1 with a relative IC50<0.8, <0.6 or <0.5 in comparison to the IC50 of monoclonal antibody 3-372.

6. The method according to claim 3, wherein the humanized antibody or the single chain Fv or Fab fragment is capable of binding to human CLEVER-1 with a relative IC50<0.5 in comparison to the IC50 of monoclonal antibody 3-372.

7. The method according to claim 3, wherein the combination of the human IgG heavy and light chain variable regions is selected from the group consisting of the following combinations:
SEQ ID NO: 14 and SEQ ID NO: 22;
SEQ ID NO: 16 and SEQ ID NO: 22;
SEQ ID NO: 16 and SEQ ID NO: 24;
SEQ ID NO: 16 and SEQ ID NO: 26;
SEQ ID NO: 16 and SEQ ID NO: 28;
SEQ ID NO: 16 and SEQ ID NO: 30;
SEQ ID NO: 18 and SEQ ID NO: 22;
SEQ ID NO: 18 and SEQ ID NO: 24;
SEQ ID NO: 18 and SEQ ID NO: 28;
SEQ ID NO: 18 and SEQ ID NO: 30;
SEQ ID NO: 20 and SEQ ID NO: 24; and
SEQ ID NO: 20 and SEQ ID NO: 30.

8. The method according to claim 3, wherein the combination of human IgG heavy and light chain variable region sequence is selected from the group consisting of the following combinations: SEQ ID NO: 16 and SEQ ID NO: 30; SEQ ID NO: 18 and SEQ ID NO: 30; and SEQ ID NO: 20 and SEQ ID NO: 30.

9. The method according to claim 2, wherein said antibody or single chain FV or Fab fragment comprises constant regions of human lgG4 heavy chain and kappa light chain with the mutations L248E and/or S241P.

10. The method according to claim 1, wherein the method removes tumor or antigen induced immunosuppression by modulating M2 macrophages into M1 macrophages.

11. A method for reducing malignant tumor growth in an individual who has a tumor comprising CLEVER-1 positive cells in the tumor microenvironment; and/or inhibiting cancer cell transmigration and metastasis formation in a tumor comprising CLEVER-1 positive cells in the tumor microenvironment, the method comprising administering a humanized antibody or single chain Fv or Fab fragment capable of binding to human CLEVER-1 to the individual, wherein said humanized antibody or single chain Fv or Fab fragment comprises the following sequences of complementarity determining regions (CDRs)

```
i) of the heavy chain
CDR 1:
                                        (SEQ ID NO: 7)
TSGMGIG, CDR 2:
                                        (SEQ ID NO: 8)
HIWWDDDKRYNPALKS,
and

CDR 3:
                                        (SEQ ID NO: 9)
HYGYDPYYAMDY;
```

```
and ii) of the light chain
CDR 1:
                                        (SEQ ID NO: 10)
TASSSVSSSYLH, CDR 2:
                                        (SEQ ID NO: 11)
RTSNLAS,
and

CDR 3:
                                        (SEQ ID NO: 12)
HQYHRSPPT.
```

12. The method according to claim 1, wherein the antibody or single chain Fv or Fab fragment binds to the epitope sequences:

```
                                        (SEQ ID NO: 1)
PFTVLVPSVSSFSSR,
and (SEQ ID NO: 2)
QEITVTFNQFTK
on human CLEVER-1.
```

13. The method according to claim 1, wherein the antibody or single chain Fv or Fab fragment binds to one or more epitope sequences selected from the group consisting of

```
                                        (SEQ ID NO: 3)
ATQTGRVFLQ, (SEQ ID NO: 4)
DSLRDGRLIYLF, (SEQ ID NO: 5)
SKGRILTMANQVL,
and (SEQ ID NO: 6)
LCVYQKPGQAFCTCR
on human CLEVER-1.
```

14. The method according to claim 1, wherein the antibody or single chain Fv or Fab fragment is administered intravenously, intraarticularly, intratumorally or subcutaneously.

15. The method according to claim 11, wherein the humanized antibody or single chain FV or Fab fragment comprises constant regions of human IgG4 heavy chain and kappa light chain.

16. The method according to claim 11, wherein the humanized antibody or single chain Fv or Fab fragment comprises a human IgG heavy chain variable region sequence comprising an amino acid sequence selected from the group consisting of SEQ ID NO: 14, SEQ ID NO: 16, SEQ ID NO 18 and SEQ ID NO: 20, and a human IgG light chain variable region comprising an amino acid sequence selected from the group consisting of SEQ ID NO: 22, SEQ ID NO: 24, SEQ ID NO: 26, SEQ ID NO: 28 and SEQ ID NO: 30.

17. The method according to claim 11, wherein the antibody or single chain Fv or Fab fragment is administered intravenously, intraarticularly, intratumorally or subcutaneously.

18. The method according to claim 1, wherein the cancer is breast cancer.

19. The method according to claim 11, wherein the individual has breast cancer.

20. The method according to claim 1, wherein the cancer is leukemia.

21. The method according to claim 11, wherein the individual has leukemia.

22. The method according to claim 1, wherein the cancer is hepatocellular carcinoma.

23. The method according to claim 11, wherein the individual has hepatocellular carcinoma.

24. The method according to claim 1, wherein the cancer is bronchogenic carcinoma.

25. The method according to claim 11, wherein the individual has bronchogenic carcinoma.

26. The method according to claim 1, wherein the cancer is melanoma.

27. The method according to claim 11, wherein the individual has melanoma.

* * * * *